(12) United States Patent
Choi et al.

(10) Patent No.: US 9,297,000 B2
(45) Date of Patent: Mar. 29, 2016

(54) ALPHA-NEOAGAROBIOSE HYDROLASE AND METHOD FOR OBTAINING A MONOSACCHARIDE USING SAME

(75) Inventors: In Geol Choi, Seoul (KR); Kyoung Heon Kim, Seongnam (KR); Sae Young Lee, Uiwang (KR)

(73) Assignee: Korea University Research and Business Foundation, Seoul (KR)

( * ) Notice: Subject to any disclaimer, the term of this patent is extended or adjusted under 35 U.S.C. 154(b) by 146 days.

(21) Appl. No.: 13/232,535

(22) Filed: Sep. 14, 2011

(65) Prior Publication Data

US 2013/0171699 A1 Jul. 4, 2013

Related U.S. Application Data

(63) Continuation of application No. PCT/KR2010/001816, filed on Mar. 24, 2010.

(30) Foreign Application Priority Data

Mar. 27, 2009 (KR) ........................ 10-2009-0026300

(51) Int. Cl.
*C12N 9/24* (2006.01)
*C12P 19/14* (2006.01)

(52) U.S. Cl.
CPC ................ *C12N 9/2402* (2013.01); *C12N 9/24* (2013.01); *C12P 19/14* (2013.01)

(58) Field of Classification Search
CPC ....................... C12N 9/2402; C12Y 302/01158
USPC .................................................. 435/195, 200
See application file for complete search history.

(56) References Cited

U.S. PATENT DOCUMENTS

| 5,418,156 A | 5/1995 | Stosz et al. |
| 2009/0053776 A1 | 2/2009 | Hutcheson et al. |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Morrice et al. (European Journal of Biochemistry, vol. 137, pp. 149-154, 1983.*
Copeland et al., UniPro Accession No. Q15UF2, Nov. 2006.*
Bentley et al., Nature 417:141-147(2002).*
Japanese Office Action for Japanese Application No. 2012-501937, issued Sep. 24, 2013.
Ekborg, N. A. et al., "Genomic and proteomic analyses of the agarolytic system expressed by Saccharophagus degradans 2-40", Applied and Environmental Microbiology, vol. 72 (5), pp. 3396-3405 (May 2006).
GenBank: GG595980.1, 2 pages.
GenBank: GG696048.1, 4 pages.
GenBank: GG695982.1, 2 pages.
GenBank: ABQCO2000019.1, 2 pages.
NCBI Reference Sequence: NC_007912.1, 2 pages.
NCBI Reference Sequence: NC_008228.1, 2 pages.
NCBI Reference Sequence: NC_003888.3, 2 pages.
NCBI Reference Sequence: NC_008571.1, 2 pages.
NCBI Reference Sequence: NC_002806.1, 2 pages.
Day et al., "Enzymatic hydrolysis of agar: purification and characterization of neoagarobiose hydrolase and p-nitrophenyl alpha-galactoside hydrolase", Can J Microbiol. Oct. 1975: 21(10):1512-8.
Weiner, Robals M., et al., "Complete Genome Sequence of the Complex Carbohydrate-Degrading Marine Bacterium, Saccharophagus degradans Strain 2-40T", PLoS Genetics, vol. 34, Issue 5. (May 2008).
Saccharophagus degradans 2-40, complete genome.
NCBI GeneBank Accession No. ABD81917 Glycosyl hydrolase family 32, N terminal [Saccharophagus degradans 2-40] (Jun. 6, 2008).
Weiner, R. M. et al., "Complete genome sequence of the complex carbohydrate-degrading marine bacterium, Saccharophagus degradans strain 2-40T", PLoS Genetics, vol. 4(5), e1000087 (May 30, 2008).

* cited by examiner

*Primary Examiner* — Richard Hutson
(74) *Attorney, Agent, or Firm* — Mintz Levin Cohn Ferris Glovsky and Popeo, P.C.; Kongsik Kim; Richard B. Emmons

(57) ABSTRACT

Provided are novel α-neoagarobiose hydrolase and a method for obtaining a monosaccharide using the same.

1 Claim, 17 Drawing Sheets

FIG. 3

```
ATG AGC GAT TCA AAA GTA AAT AAA AAA TTG ACT AAA GCT AGC CTG CCA GCG ATA GAG CGG  < 60
 M   S   D   S   K   V   N   K   K   L   T   K   A   S   L   R   A   I   E   R

GGC TAC GAT GAA AAG GGC CCT GAA TGG CTG TTT GAG TTT GAC ATT ACC CCA GAA AAA GGC  < 120
 G   Y   D   E   K   G   P   E   W   L   F   E   F   D   I   T   P   E   K   G

GAC TTA GCC TAC GAA GAA GGC GTA ACT CGT CGA GAC CCC AGC GCA GTA TAA AAG GTG GAC  < 180
 D   L   A   Y   E   E   G   V   T   R   R   D   P   S   A   V   L   K   V   D

GAC GAA TAT CAC GTT TGG TAC ACC AAG GGC GAA GGT GAA ACA GTA GGC TTC GGC AGC GAC  < 240
 D   E   Y   H   V   W   Y   T   K   G   E   G   E   T   V   G   F   G   S   D

AAG CCC GAA CAC AAA GTC TTG CCA TCC CAT AAA ACA GAA GTT TGG CAC GCC ACC TCT AAA  < 300
 N   P   E   H   K   V   F   P   S   H   K   T   E   V   W   H   A   T   S   K

GAT AAG ACT ACT TGG AAA GAA ATT GGC CCT GCC ACA CAA CGC GGG GCA GCT GGC GCA TAC  < 360
 D   K   T   T   W   K   E   I   G   P   A   T   Q   R   G   A   A   G   A   Y

GAT GAC CCT GGA CTC TTG ACC CCC GAA CTC CTC GGC CAC AAG GGC ACC TAC TAC GTT GTA  < 420
 D   D   P   G   L   L   T   P   E   L   L   G   H   K   G   T   Y   Y   L   V

TAT CAA ACC GTA AAA GCC CCC TAC TTA AAC CGA AGC CTA GAC CAT ATA GCC ACC GCA TAC  < 480
 Y   Q   T   V   K   A   P   Y   L   N   R   S   L   D   H   I   A   T   A   Y

AGC GAT TCC CCT TTT GGC CAA TGG AGC AAA TGG GAT GCG CCA ATT TTA AGC CCA GAA AAT  < 540
 S   D   S   P   F   G   Q   W   S   K   W   D   A   P   I   L   S   P   E   N

GAC GGC GTT TGG GAT ACC GAC GAA GAT AAT CGA TTT CTA GTA AAA GAG AAA GGC AGT TTC  < 600
 D   G   V   W   D   T   D   E   D   N   R   F   L   V   K   E   K   G   S   F

GAC AGC CAC AAA GTA CAC GAC CCC TCC TTA ATG CCT TTC AAC AAT CGC CAC CTG TAC  < 660
 D   S   H   K   V   H   D   P   S   L   M   P   F   N   N   R   H   L   Y

TAC AAA GGC GAG ACT ATG GGC GAA AGC ATG AAC ATG GGC GGC AGA GAA ATA AAA CAC GGT  < 720
 Y   K   G   E   T   M   G   E   S   M   N   M   G   G   R   E   I   K   H   G

GTA GCC ACT GAC TCG CCA CTT GGC GCC TAC ACC AAA AGC GAA TAC AAC CCT ATT ACC  < 780
 V   A   T   D   S   P   L   G   A   Y   T   K   S   E   Y   N   P   I   T

AAC AGT GGC CAT GAA GTC GCC GTA TGG CCC TAC AAA GGT GGA ATG GCC ACC ACG CTA ACC  < 840
 N   S   G   H   E   V   A   V   W   P   Y   K   G   G   M   A   T   T   L   T

ACC GAC GGG CCA GAA AAA AAC AGC TGC CAG TGG GCA GAA GAC GGC ATT AAC TTT GAC ATT  < 900
 T   D   G   P   E   K   N   S   C   Q   W   A   E   D   G   I   N   F   D   I

ATG TCG CAT ATA AAA GGC GCA CCA GAA GGA GGT TTT TTC AGA CCA GAA AGC GAC AGC  < 960
 M   S   H   I   K   G   A   P   E   G   G   F   F   R   P   E   S   D   S

GAC GAC CCT ATA AGC GGC ATC GAA TGG GGC CTA AGC CAC AAG TAC GAC GCC AGC TGG AAC  < 1020
 D   D   P   I   S   G   I   E   W   G   L   S   H   K   Y   D   A   S   W   N

TGG AAC TAT CCA TGC TTC CTC AAA ACG CGT CGA CAA GTC TTA GAT GCA GGT AGC TAC CAG  < 1080
 W   N   Y   P   C   F   L   K   T   R   R   Q   V   L   D   A   G   S   Y   Q

CAA ACA GGC GAT TCC GGA GCA GTA TAA  < 1107
 Q   T   G   D   S   G   A   V   *
```

FIG. 7A

```
*****************************
SUMMARY OF MOTIFS
*****************************
       Combined block diagrams: non-overlapping sites with p-value < 0.0001
                                                                                                  Saccharophagus degradans-derived
                                                                                                  Neoagarobiose hydrolase
SEQUENCE NAME              COMBINED P-VALUE   MOTIF DIAGRAM
---------------            ---------------    -------------
Q21HB2|Q21HB2_SACD2        2.36e-213          36_[40(1.22e-13)]_[6(9.94e-19)]_7_[14(8.72e-22)]_[5(6.24e-11)]_4_[17(2.16e-14)]_[2(2.71e-
                                              14)]_[34(7.85e-12)]_1_[3(1.87e-13)]_1_[16(2.90e-12)]_2_[7(1.39e-58)]_[3(9.17e-
                                              26)]_1_[4(8.34e-51)]_1_[20(3.74e-20)]_29
Q15UF2|Q15UF2_PSEA6        8.93e-207          34_[40(8.17e-13)]_[6(2.04e-16)]_7_[14(4.81e-21)]_[5(1.26e-08)]_4_[17(5.89e-15)]_[2(7.58e-
                                              15)]_[34(3.21e-12)]_1_3_[1(4.14e-12)]_1_[16(1.58e-13)]_2_[7(7.82e-58)]_[3(5.05e-
                                              22)]_1_[4(5.14e-51)]_1_[20(1.13e-21)]_24
Q93PB9|Q93PB9_9SPHI        0.00e+00           5_[24(9.01e-05)]_[32(7.78e-42)]_7_[40(4.66e-21)]_7_[14(8.10e-23)]_[5(1.06e-
                                              10)]_4_[17(1.86e-16)]_[2(1.61e-11)]_[34(1.12e-12)]_3_[1(2.85e-14)]_1_[16(4.11e-
                                              14)]_2_[7(7.03e-49)]_[3(4.24e-20)]_1_[4(1.50e-51)]_[20(8.55e-08)]_[48(6.95e-20)]_1_8
B5CY74|B5CY74_9BACE        0.00e+00           [24(6.50e-06)]_1_2_[32(3.05e-26)]_7_[40(1.22e-13)]_[34(2.08e-12)]_3_[1(3.19e-13)]_1_[16(1.13e-
                                              12)]_4_[17(2.17e-16)]_1_2_[6(3.30e-13)]_[34(3.30e-55)]_1_[20(7.66e-24)]_7_[14(1.48e-25)]_[5(8.41e-
                                              13)]_2_[7(8.06e-53)]_[3(5.61e-21)]_1_[4(3.30e-55)]_1_[48(5.76e-23)]_4
A0M245|A0M245_GRAFK        0.00e+00           2_[38(2.13e-18)]_4_[32(9.35e-38)]_8_[40(1.22e-13)]_7_[6(3.65e-21)]_7_[14(1.48e-25)]_[5(5.88e-
                                              10)]_4_[17(4.57e-16)]_[2(5.05e-08)]_[34(2.43e-13)]_3_[1(2.03e-14)]_1_[16(3.04e-
                                              13)]_2_[7(1.40e-45)]_[3(1.96e-20)]_1_[4(2.03e-54)]_3_[20(2.81e-17)]_[48(8.04e-25)]_2
A4AR39|A4AR39_9FLAO        0.00e+00           12_[32(8.07e-37)]_8_[40(1.22e-13)]_[6(3.21e-19)]_7_[14(1.48e-25)]_[5(3.26e-10)]_4_[17(8.68e-
                                              15)]_[2(1.69e-08)]_[34(7.75e-14)]_3_[1(3.57e-14)]_1_[16(1.71e-14)]_2_[7(1.49e-47)]_[3(5.08e-
                                              18)]_1_[4(2.86e-57)]_7_[20(2.97e-23)]_[48(2.75e-24)]_2
C6J3P3|C6J3P3_9BACL        0.00e+00           14_[43(2.34e-20)]_2_[6(6.28e-24)]_7_[34(1.97e-13)]_3_[1(8.52e-14)]_1_[16(2.75e-16)]_2_[7(7.00e-57)]_[3(3.85e-
                                              22)]_1_[4(3.44e-57)]_1_[20(1.48e-30)]_35
C6JDD4|C6JDD4_9FIRM        6.92e-205          15_[43(1.12e-18)]_2_[6(5.24e-19)]_7_[14(6.45e-23)]_[5(1.53e-08)]_4_[17(1.59e-16)]_[2(4.05e-
                                              14)]_[34(6.59e-12)]_1_3_[1(1.29e-13)]_1_[16(3.81e-12)]_2_[7(9.02e-53)]_[3(3.51e-
                                              20)]_1_[4(1.06e-50)]_1_[20(2.21e-21)]_23
C6J3I3|C6J3I3_9BACL        3.63e-214          16_[43(2.09e-21)]_2_[6(2.46e-21)]_7_[14(2.49e-21)]_[5(1.70e-09)]_4_[17(1.16e-16)]_[2(9.35e-
                                              16)]_[34(4.48e-06)]_3_[1(8.52e-14)]_1_[16(9.63e-15)]_2_[7(1.01e-52)]_[3(6.97e-
                                              21)]_1_[4(1.50e-51)]_1_[20(2.35e-27)]_36
Q15XP8|Q15XP8_PSEA6        8.14e-202          36_[32(8.85e-26)]_19_[6(1.05e-16)]_7_[14(4.05e-23)]_[5(3.60e-11)]_4_[17(1.12e-12)]_[2(1.83e-
                                              12)]_[34(2.76e-11)]_3_[1(1.45e-11)]_1_[16(5.10e-13)]_2_[7(1.93e-51)]_[3(6.68e-
                                              18)]_1_[4(1.73e-42)]_1_[20(2.81e-17)]_7_[48(6.74e-13)]_19
Q9RKF6|Q9RKF6_STRCO        9.07e-195          16_[43(7.27e-18)]_2_[6(8.33e-20)]_7_[14(7.23e-23)]_[5(6.78e-09)]_4_[17(3.76e-17)]_[2(4.05e-
                                              13)]_[34(6.20e-11)]_3_[1(2.98e-11)]_1_[16(3.74e-13)]_2_[7(2.46e-48)]_[3(2.99e-
                                              16)]_1_[4(6.75e-53)]_1_[20(2.85e-22)]_39
D0PR06|D0PR06_9SPHI        2.76e-101          4_[24(2.79e-09)]_31_[43(9.83e-18)]_5_[6(1.59e-18)]_9_[14(3.09e-06)]_[5(2.91e-
                                              11)]_19_[2(7.06e-12)]_15_[3(2.41e-12)]_1_[30(6.21e-16)]_10_[3(9.50e-17)]_1_[4(3.61e-
                                              38)]_2_[20(2.98e-05)]_60
A6DFN5|A6DFN5_9BACT        7.43e-91           25_[45(3.59e-05)]_6_[43(2.52e-16)]_2_[6(2.53e-18)]_9_[14(2.01e-05)]_[5(2.81e-
                                              10)]_20_[2(5.32e-12)]_14_[14(4.51e-12)]_1_[16(3.16e-09)]_1_[30(6.15e-13)]_12_[3(5.19e-
                                              16)]_1_[4(7.99e-42)]_2_[20(6.95e-05)]_62
```

```
A7V0K0|A7V0K0_BACUN    1.31e-135    1_[38(3.14e-28)]_13_[27(1.28e-20)]_4_[5(8.89e-10)]_2_[29(8.31e-14)]_12(2.15e-
                                    15)]_5_[1(2.14e-13)]_14_[8(4.42e-14)]_1_[19(1.19e-32)]_2_[13(8.50e-15)]_6_[3(4.56e-
                                    15)]_7_[22(5.72e-20)]_42

A7V878|A7V878_BACUN    7.38e-159   [24(8.09e-07)]_5_[30(1.79e-09)]_8_[5(3.26e-10)]_4_[29(1.07e-11)]_2_[3.11e-14)]_1_[26(8.25e-
                                    17)]_[1(2.28e-14)]_[33(1.25e-16)]_1_[8(1.85e-16)]_9_[11(4.73e-44)]_8_[13(1.29e-
                                    20)]_6_[3(2.17e-18)]_29_[10(4.75e-28)]_13

B5JL78|B5JL78_9BACT    2.95e-42    28_[47(1.89e-11)]_1_[6(1.09e-07)]_9_[5(8.89e-10)]_24_[2(1.45e-09)]_7_[11(1.48e-
                                    06)]_11_[8(9.44e-06)]_38_[13(1.08e-20)]_33_[18(5.43e-06)]_4_[31(4.50e-16)]_161_[44(6.28e-
                                    05)]_25

A3XIS8|A3XIS8_9FLAO    7.01e-98    29_[27(1.62e-18)]_9_[5(1.50e-09)]_7_[29(3.42e-11)]_[2(1.76e-11)]_5_[1(3.80e-
                                    12)]_9_[30(6.61e-15)]_5_[19(8.76e-31)]_11_[8(1.20e-10)]_4_[3(5.94e-13)]_7_[22(4.67e-
                                    18)]_10_[46(7.75e-05)]_7

A5FIA6|A5FIA6_FLAJ1    4.19e-116   [24(1.59e-18)]_7_[27(3.42e-20)]_9_[5(2.96e-08)]_7_[29(1.85e-10)]_12_[2(2.29e-11)]_5_[1(8.52e-
                                    14)]_14_[8(7.46e-12)]_1_[19(7.23e-27)]_1_[5(13(4.48e-12)]_6_[3(1.35e-15)]_8_[22(1.08e-19)]_38

A3HZ01|A3HZ01_9SPHI    9.27e-67    47_[8(2.40e-16)]_1_[9(8.79e-23)]_1_[36(4.68e-09)]_1_[2(5.32e-12)]_37_[3(1.52e-
                                    12)]_12_[8(1.25e-07)]_5_[3(9.23e-09)]_1_3_[30(6.47e-12)]_7_[5(1.26e-08)]_24_[15(1.89e-06)]_5

Q6ZA95|Q6ZA95_ORYSJ    7.39e-44    51_[2(1.69e-07)]_5_[37(4.08e-07)]_34_[2(7.33e-05)]_27_[37(9.45e-15)]_32_[8(7.46e-
                                    12)]_7_[5(4.90e-09)]_4_[17(5.22e-06)]_2_[8(5.89e-05)]_3_[1(1.28e-09)]_2_[16(1.31e-
                                    11)]_22_[42(3.22e-25)]_3

A2YVH9|A2YVH9_ORYSI    4.62e-45    51_[2(1.69e-07)]_5_[37(4.08e-07)]_34_[2(7.33e-05)]_26_[37(9.45e-15)]_32_[8(7.46e-
                                    12)]_7_[5(4.90e-09)]_4_[17(5.22e-06)]_2_[8(5.89e-05)]_3_[1(1.28e-09)]_2_[16(1.31e-
                                    11)]_22_[42(3.22e-25)]_3

B5HR57|B5HR57_9ACTO    1.48e-58    2_[24(5.16e-06)]_98_[37(8.02e-10)]_73_[30(5.06e-11)]_35_[45(9.40e-12)]_37_[44(9.14e-
                                    14)]_87_[27(3.16e-06)]_10_[5(4.32e-11)]_19_[2(8.80e-10)]_5_[1(5.32e-15)]_17_[27(7.73e-
                                    14)]_22_[6(1.16e-09)]_10_[3(1.44e-10)]_76

A3TN34|A3TN34_9MICO    1.46e-31    24_[30(7.29e-16)]_14_[37(4.15e-14)]_3_[17(7.86e-07)]_1_[8(8.86e-12)]_10_[5(8.37e-
                                    09)]_63_[41(3.20e-12)]_8_[8(1.19e-05)]_[2(1.59e-07)]_[26_[2(4.91e-05)]_29

B9XBB3|B9XBB3_9BACT    5.27e-60    38_[6(1.16e-07)]_10_[5(3.24e-08)]_2_[29(2.39e-10)]_1_[2(6.30e-13)]_10_[1(5.97e-
                                    08)]_8_[6(6.31e-05)]_38_[13(6.14e-20)]_8_[3(5.94e-13)]_12_[8(1.20e-10)]_[31(1.73e-
                                    08)]_75_[25(1.11e-05)]_43_[37(2.83e-10)]_8_19(6.33e-05)]_3

A7ALA4|A7ALA4_9PORP    8.90e-157   [24(7.01e-20)]_6_[27(1.50e-09)]_6_[5(2.36e-12)]_2_[29(1.44e-11)]_[2(5.32e-12)]_11_[1(5.68e-
                                    13)]_9_[30(8.36e-13)]_32_[13(1.03e-23)]_8_[3(2.04e-15)]_[18(4.82e-31)]_1_[31(1.26e-
                                    19)]_72_[25(1.04e-31)]_16_[46(6.74e-20)]_5_[37(7.02e-13)]_43

C6Y048|C6Y048_PEDHD    5.48e-115   2_[38(1.53e-17)]_1_[27(5.24e-19)]_7_[5(1.08e-07)]_2_[29(3.36e-10)]_[2(2.29e-11)]_5_[3(4.17e-
                                    10)]_4_[30(1.29e-16)]_5_[19(4.36e-30)]_5_[13(5.02e-12)]_6_[3(1.20e-16)]_8_[22(6.27e-
                                    20)]_27_[2(3.12e-05)]_2

B7BE88|B7BE88_9PORP    3.71e-157   [24(7.69e-20)]_6_[27(4.58e-10)]_6_[5(2.36e-12)]_2_[29(1.44e-11)]_[2(5.32e-12)]_11_[1(5.68e-
                                    13)]_9_[30(8.36e-13)]_32_[13(2.20e-23)]_8_[3(2.04e-15)]_[18(4.82e-31)]_1_[31(1.26e-
                                    19)]_72_[25(1.04e-31)]_16_[46(6.74e-20)]_5_[37(2.34e-13)]_43

A0Z6Z9|A0Z6Z9_9GAMM    2.06e-35    [50(2.14e-10)]_13_[45(7.12e-07)]_27_[17(3.11e-10)]_29_[3(1.30e-09)]_7_[6(1.48e-
                                    08)]_22_[5(5.88e-10)]_16_[27(4.48e-06)]_12_[37(1.69e-12)]_16_[30(4.44e-12)]_14
```

\* Above Motif Diagram represents:
...Sequence Spacing_[Motif(p-value)]_Sequence Spacing_[Motif(p-value)]_...

FIG. 8

Regular Expression of Motifs

Motif 1   [IV]GVA[VA]A[SED]EP[KGP]WF[IKE][TKR]
Motif 2   [ATN]PE[IV]LY[EH]DN[GK]K[YF]Y[LM][IY][IY]F]
Motif 3   VQVA[TH]AS[DE]D[IP][IL]EGP[YF]TKSE[KH][IV]
Motif 4   NSGH[ET]V[CM]L[FW]F[PQ]IYF[KG]DG[IM]A[AS]L[LI]TTDGP[EK]NT[IQ]YW[TA]PE[DQ]GR[V]NFE[DH]M[KH]AS[IVH][RK]G[NI]AP[S]PE[PH]A
Motif 5   [AY]TSKD[GL]I[VJ]I]TN[WE]
Motif 6   V[KR][DE]P[SP]S[V][L][KE]V[DI]GD[S]xY[YIVM]W[YST]
Motif 7   DN[FK]FLLT[IV]K[VIS]H[KQ]G[IQ]OS[FD]S[HL]KVH[DP][CT]L[FL]FP[IF]Y[LN]R[IG]N[I]KQB[IF]YW[L]YRGE[QR]T[MG]EE[MN]T[FAM]G[IG][HE]T[JIT][KR]
Motif 14  GFG[TG]DG[TD]P[ED]N[DA]KVFPWDR[CS][DE][IV]W[YF]
Motif 16  [DE]K[QA]EK[P]LLE[RS]P[GS]HDTN[GE]SWD[GD]
Motif 17  [IV][GR]GE[KP]IG[SA]H[YF]DDRJ[SA]YF
Motif 20  GLP[I]YPN[RN]PST[IE]LP[DA]DE[S][DK]R][ER]SPL[LT]EA[IG][L]IREJWG[LC]SH[DK]N[I]Y[V]ND[H][SA][N][SK][WD]
Motif 34  OE TVAH VI[QK][LSA]PYT[TL]N[JN]VL[RG]TV
Motif 40  PLKGDLAYEEG

ALPHA-NEOAGAROBIOSE HYDROLASE AND METHOD FOR OBTAINING A MONOSACCHARIDE USING SAME

CROSS-REFERENCE TO RELATED APPLICATION

This application is a continuation of PCT/KR2010/001816 filed Mar. 24, 2010, which claims the benefit of Korean Application No. 10-2009-0026300 filed Mar. 27, 2009, the entire contents of which applications are incorporated herein by reference.

SEQUENCE LISTING

The instant application contains a Sequence Listing which has been submitted in ASCII format via EFS-Web and is hereby incorporated by reference in its entirety. Said ASCII copy, created on Jul. 1, 2014, is named U.S. Ser. No. 13/232,535_SequenceListing_ST25.txt and is 47,301 bytes in size.

TECHNICAL FIELD

The present invention relates a novel alpha ($\alpha$)-neoagarobiose hydrolase and a method for obtaining a monosaccharide using the same.

BACKGROUND ART

In recent years, there has been an increasing demand for development of a new alternative energy for reducing carbon dioxide all over the world due to the exhaustion of raw petroleum and increase in their prices which will occur in the near future, as well as the global warming caused by an increased amount of carbon dioxide emitted into the air. Bioenergy produced from biomass, which is one of earth resources that are reusable and rich among a variety of alternative energies, has come into the spotlight as a main renewable energy, which meets the above-described requirements. Particularly, bioethanol has been considered to be an alternative to a transportation fuel which is currently on high demand. For example, the use of bioethanol has already been obliged by the law in developed countries including the United States. Since raw materials currently used to produce bioethanol are limited to sugar, starch and the like derived from maize or other food resources (first-generation bio-fuel), they compete with mankind food resources, which results in an increase in price of international grains. As an alternative to solve these problems, a new land biomass (land biomass or lignocellulosic biomass??) (second-generation bio-fuel) or marine algal biomass (third-generation bio-fuel), which does not compete with the food resources, has also come into the spotlight as a next-generation bioenergy resource, and technologies for generating bio energy using the biomass has been on active research.

Since the marine (algal)biomass has a high content of polysaccharide usable by microorganisms, compared to the land (lignocellulosic)biomass, and is free from lignin, the marine biomass may be relatively easily pretreated, and harvested several times a year. In particular, since the Korean peninsula is surrounded by the sea on three sides except for the northern part, seaweeds may be used as a bio-resource, and their total annual yield is over 13,754 tons in 2006. In this aspect, the Republic of Korea belong to global seaweeds-producing countries including China, Japan and North Korea, but the usability of seaweeds other than edible resources is in a poor state (Korean fishery production statistics in 2006 by the Agriculture and Fisheries Production Statistics Division of the Population and Social Statistics Bureau in the Korea National Statistical Office).

Recently, much research on production of bioenergy from seaweeds has been conducted in Japan and Korea. In the name of the "Ocean Sunrise Project," the Tokyo Fisheries Promotion Foundation has made a plane to produce five billion liters of fuel ethanol by farming a large amount of seaweeds in 4.47 million $km^2$ of the exclusive economic zone and unused sea areas in the sea belt of Japan (Aizawa M et al., Seaweed bioethanol production in Japan—The Ocean Sunrise Project, OCEANS Conference, Sep. 29-Oct. 4, 2007, Vancouver, Canada). In Korea, a great interest has been focused in production of seaweeds since an ocean bio-fuel was included in the field of novel renewable energy, which is one of the 17 New Growth-driving Industries finally issued by the Korean Government on January of 2009. According to the presentation of development and research for technical exploration and utilization of ocean biomass issued by the Ministry for Food, Agriculture, Forestry and Fisheries in 2009, when seaweeds were cultured in a sea area of a regular square with 71 km each side to produce bioethanol, the bioethanol may be produced at an amount of 3.774 billion liters a year, which will replace 31.4% of an expected consumption of volatile oils in Korea in 2030.

Among the seaweeds recently known in the art, there has been active research on the use of red seaweed biomass (for example, *Gelidium amansii*) as a source material. Red seaweeds accounts for at least 70% of the total dry weight of polysaccharides, which may be converted into fermentable sugars that are usable by microorganisms. In particular, a main component of the polysaccharide derived from the red seaweed biomass is agar which accounts for approximately 60% of the total dry weight. Therefore, the red seaweed biomass has been considered to be a main resource for production of bioenergy. Agar polysaccharide is a polymer obtained by binding D-galactose and 3,6-anhydro-L-galactose (hereafter, abbreviated as "AHG"), which are used as monomer units, through $\alpha$-1,3-linkage or $\beta$-1,4-linkage (Duckworth, M. and W. Yaphe (1971) *Carbohydrate Research* 16, 435-445) (see FIG. 1).

It was known that microorganisms using the agar polysaccharide as a carbon source use $\beta$-agarase or $\alpha$-agarase to cleave the agar polysaccharide into smaller oligosaccharides. In this case, the oligosaccharides are finally degraded into $\alpha$-neoagarobiose (or, $\alpha$-1,3-D-galactosyl-3,6-anhydro-L-galactose) by the $\beta$-agarase, and finally degraded into $\beta$-agarobiose (or, $\beta$-1,4-anhydro-L-galactosyl-D-galactose) by the $\alpha$-agarase. It was known that, when a degradation product of the $\beta$-agarase is neoagarobiose, the neoagarobiose should be converted into galactose so as to be metabolized by a microorganism, and thus $\alpha$-neoagarobiose hydrolase cleaving an $\alpha$-1,3 linkage is necessarily required for convention of the neoagarobiose into the galactose (Ekborg, N. A. et al (2005) *Int. J. Syst. Evol. Microbiol.* 55, 1545-1549; Ekborg, N. A. et al., (2006) *Appl. Environ. Microbiol.* 72, 3396-3405). However, an enzyme cleaving the $\alpha$-1,3 linkage of neoagarobiose in *S. degradas* was not found until now (Ekborg, N. A. et al. (2006) *Appl. Environ. Microbiol.* 72, 3396-3405).

It was reported that $\beta$-agarase that produces oligoagarosaccharides from agarose in a microorganism is produced by many microorganisms such as, for example, a *Pseudomonas* sp. strain (Ha, J. C. et al. (1997) *Biotechnol. Appl. Biochem.* 26:1-6), an *Alteromonas* sp. strain (Potin, P., et al. (1993) *Eur. J. Biochem.* 214:599-607), an *Agarivorans* sp. strain (Ohta, Y. et al. (2005) *Biotechnol. Appl. Biochem.* 41:183-191), a *Pseudoalteromonas* sp. strain (Belas, R. (1989) *J. Bacteriol.*

171:602-605), a *Microsilla* sp. strain (Zhong, Z. et al. (2001) *Appl. Environ. Microbiol.* 67:5771-5779), and a *Vibrio* sp. strain (Aoki, T. et al. (1990) *Eur. J. Biochem.* 187:461-465).

When agar polysaccharide derived from red seaweed was used as a resource for production of bioenergy, the agar polysaccharide is necessarily converted into fermentable sugars, which can be actually used by a microorganism through a multiple pretreatment procedures. The conversion of the agar polysaccharide into fermentable monosaccharides may be performed through two processes: chemical pretreatment and biological pretreatment. First, a chemical method using acid hydrolysis is a relatively simple process, but a biomass composed of polysaccharides is chemically pretreated at a high temperature to mass-produce toxic by-products such as furfural and hydroxymethylfurfural (HMF), and to yield a mixture of randomly cleaved monosaccharide and oliogosaccharide (Pickering et al., 1993, Journal of Applied Phycology 5: 85-91; Armis'en, 1995). On the contrary, the biological pretreatment and saccharification methods using an enzyme such as β-agarase has an advantage in that they are environment-friendly methods performed at a room temperature to obtain a fermentable sugar such as galactose, but a currently commercially available enzyme is limited to β-agarase and a final product of the β-agarase is disaccharide (neoagarobiose or agarobiose) which may not used by conventional microorganisms.

Neoagarobiose produced from a reaction of the β-agarase should be necessarily converted into a fermentable monosaccharide such as galactose for use in production of bioenergy. In this case, α-neoagarobiose hydrolase is required. Therefore, in a final step of the effective biological (enzymatic) pretreatment and saccharification processes to use a red algal biomass as a resource for production of bioenergy such as bioethanol, α-neoagarobiose hydrolase is necessarily required. Also, AHG which is produced with galactose as degradation products of neoagarobiose was not commercially available, and may be purchased only as D-AHG, which is, however, very expensive (200 pounds (G.B.)/100 mg as of 2009, Dextra Laboratories). Therefore, it is possible to mass-produce an expensive, rare monosaccharide, AHG, from agarose using the enzyme of the present invention.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention is designed to solve the above-described problems, and therefore it is an object of the present invention to provide an enzyme which is necessarily required for conversion of fermentable monosaccharide, galactose, to produce a bioenergy.

Also, it is another object of the present invention to provide a method for converting neoagarobiose as a substrate into monosaccharides such as galactose and AHG.

In order to solve the above-described problems, the present invention provides α-neoagarobiose hydrolase (hereinafter, referred to as "α-NABH") selected from the group consisting of SEQ ID NO: 1 to SEQ ID NO: 11.

In one preferred embodiment of the present invention, enzymes having the α-neoagarobiose hydrolase activity include proteins having the α-neoagarobiose hydrolase activity, such as mutant proteins produced by at least one mutation such as substitution, deletion, translocation or addition of the enzyme, as well as amino acid sequences set forth in SEQ ID NO: 1 to SEQ ID NO: 11, all of which are included in the scope of the present invention. Preferably, the enzymes of the present invention include amino acid sequences having a sequence identity of 80% or more, 85% or more, 90% or more, 93% or more, 94% or more, 95% or more, 96% or more, 97% or more, 98% or more and 99% or more with the amino acid sequences set forth in SEQ ID NO: 1 to SEQ ID NO: 11.

According to the present invention, a polypeptide having a sequence identity of certain percentage (for example, 80%, 85%, 90%, 95%, or 99%) with another sequence means that the two sequences has the same amino acid residues at any percentage when they are aligned to each other. The alignment and percentage homology or identity may be determined using any suitable software program known in the art, for example, those described in CURRENT PROTOCOLS IN MOLECULAR BIOLOGY (F. M. Ausubel, et al., (eds) 1987 Supplement 30 section 7.7.18). A preferred program includes GCG Pileup programs, for example FASTA (Pearson, et al., 1988 Proc. Natl. Acad. Sci. USA 85: 2444-2448), and BLAST (BLAST Manual, Altschul et al., Natl. Cent. Biotechnol. Inf., Natl Lib. Med. (NCIB NLM NIH), Bethesda, Md., and Altschul et al., 1997 NAR25:3389-3402). Another preferred alignment program is ALIGN Plus (Scientific and Educational Software, PA), which preferably use basic parameters. Still another preferred sequence software program which may be used herein is a TFASTA Data Searching program available for Sequence Software Package Version 6.0 (Genetics Computer Group, University of Wisconsin, Madison, Wis.).

According to one embodiment of the present invention, the enzyme may be obtained from *Saccharophagus degradans* (*S. degradans*) and the like, but the present invention is not limited thereto.

The *S. degradans* of the present invention may be typically purchased (*S. degradans* ATCC 43961), but the present invention is not limited thereto. Therefore, the *S. degradans* of the present invention may be available through various methods.

Also, the present invention provides a gene coding for the enzyme of the present invention.

According to one embodiment of the present invention, the gene may be set forth in SEQ ID NO: 12, but the present invention is not limited thereto.

According to one embodiment of the present invention, the gene may also be obtained from *S. degradans*, but the present invention is not limited thereto.

Also, the present invention provides a method for preparing the enzyme of the present invention. Here, the method includes cultivating *S. degradans*; and extracting the enzyme of the present invention from a culture solution.

In addition, the present invention provides a method for preparing galactose and AHG. Here, the method includes degrading α-neoagarobiose using the enzyme of the present invention; and extracting galactose and AHG from the degradation product.

Furthermore, the present invention provides α-neoagarobiose hydrolase including 13 motifs such as motifs 1, 2, 3, 4, 5, 6, 7, 14, 16, 17, 20, 34 and 40 among the motifs selected from the group consisting of motifs 1 to 50 (total 50 motifs) as shown in FIG. 8, and more preferably α-neoagarobiose hydrolase essentially including motifs 7 and 34 among the 50 motifs as shown in FIG. 8.

A protein motif may be represented by a regularly repeating pattern, and the expression of the pattern is typically represented by a regular expression; See, the World Wide Web (www) at expasy.ch/prosite/prosuser.html; for example:

PA[AC]-x-V-x(4)-{ED}.

This pattern is analyzed, as follows: [Ala or Cys]-any-Val-any-any-any-any-{any but Glu or Asp}

PA<A-x-[ST](2)-x(0,1)-V.

The pattern should be positioned at the N-terminus of a sequence ("<"), and is analyzed, as follows: Ala-any-[Ser or Thr]-[Ser or Thr]-(any or none)-Val; Sigrist C. J. A., Cerutti L., Hulo N., Gattiker A., Falquet L., Pagni M., Bairoch A., Bucher P. PROSITE: a documented database using patterns and profiles as motif descriptors. Brief Bioinform. 3:265-274 (2002); Sigrist C. J. A., De Castro E., Langendijk-Genevaux P. S., Le Saux V., Bairoch A., Hulo N. ProRule: a new database containing functional and structural information on PROSITE profiles. Bioinformatics. 2005 Nov. 1; 21(21):4060-6. Epub 2005 Aug. 9; Timothy L. Bailey, Nadya Williams, Chris Misleh, and Wilfred W. Li, MEME: discovering and analyzing DNA and protein sequence motifs, Nucleic Acids Research, Vol. 34, pp. W369-W373, 2006).

According to the present invention, a base sequence and a protein sequence of novel α-neoagarobiose hydrolase are disclosed. In particular, since α-neoagarobiose hydrolase is necessarily used to produce AHG and galactose from agar polysaccharides during an enzymatic conversion process of a biomass into fermentable sugars in the recent bioenergy production using seaweed biomass as described above, reduction in costs and an increase in yield may be expected through the biomass pretreatment. Also, when an α-NABH gene is introduced into yeast or bacterium producing a bio-fuel, the biofuel may be expected to be directly produced from agar or neoagarobiose. Furthermore, since α-neoagarobiose hydrolase is used in a process of producing higher value-added monosaccharides, for example, galactose and AHG, from an ocean biomass, it is possible to produce a useful material.

BRIEF DESCRIPTION OF DRAWINGS

The above and other features of the present invention will now be described in detail with reference to certain exemplary embodiments thereof illustrated the accompanying drawings which are given hereinbelow by way of illustration only, and thus are not limitative of the present invention, and wherein:

FIG. 3 shows a base sequence (SEQ ID NO: 4) and a protein sequence (SEQ ID NO: 12) of a gene screened according to one exemplary embodiment of the present invention.

FIGS. 7A through 7D show analytic results of motifs of a homologous protein including α-neoagarobiose hydrolase.

FIG. 8 shows α-neoagarobiose hydrolase-specific motifs (SEQ ID NO: 13 to SEQ ID NO: 25).

FIG. 9 shows sequences of proteins (SEQ ID NO: 2 and SEQ ID NO: 5 to SEQ ID NO: 9) including all the α-neoagarobiose hydrolase-specific motifs confirmed in FIG. 8.

FIG. 10 shows sequences of proteins (SEQ ID NO: 3, SEQ ID NO: 10, SEQ ID NO: 11, SEQ ID NO: 1, and SEQ ID NO: 4) including the α-neoagarobiose hydrolase-specific motifs confirmed in FIG. 8.

FIG. 11 shows a multiple sequence alignment using the ten sequences obtained in FIGS. 9 and 10 and an amino acid sequence of the α-neoagarobiose hydrolase (SEQ ID NO: 6, SEQ ID NO: 8, SEQ ID NO: 2, SEQ ID NO: 7, SEQ ID NO: 1, SEQ ID NO: 4, SEQ ID NO: 9, SEQ ID NO: 3, SEQ ID NO: 11, SEQ ID NO: 10, and SEQ ID NO: 5).

DETAILED DESCRIPTION OF THE DISCLOSURE

Figure 1:
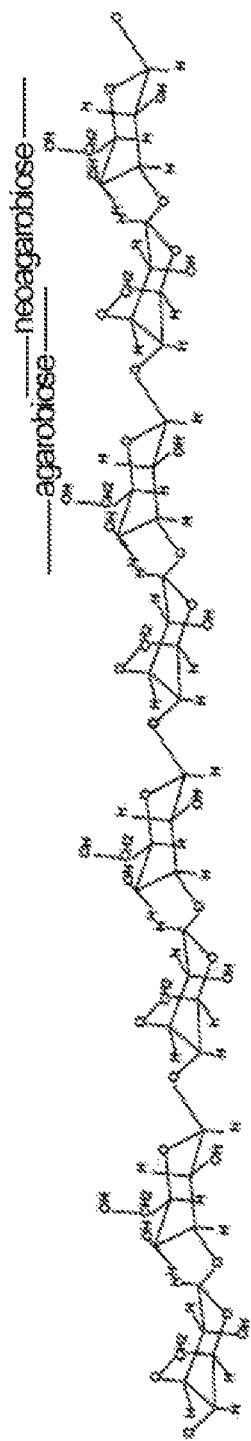
FIG. 1 is a diagram showing a structure of agar polysaccharide.
Figure 2:
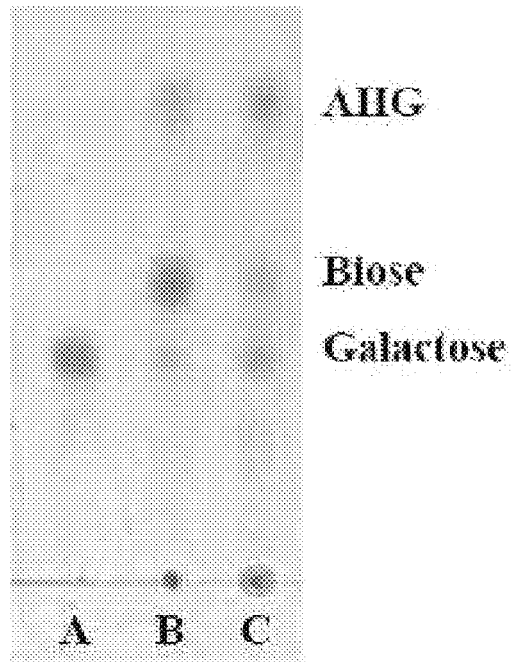
FIG. 2 is a photograph showing reaction products by an endogenous crude enzyme obtained from S. degradans 2-40 using thin layer chromatography (TLC). Here, Lane A represents a galactose standard; Lane B represents a culture solution obtained by incubating 0.25% (w/v) agarose with an endogenous enzyme; and Lane C represents a culture solution obtained by incubating 0.3% (w/v) Geladium (red seaweed) powder with an endogenous enzyme. An enzymatic reaction was performed at 30° C. in 20 mM Tris-HCl (pH6.8) for 12 hours.
Figure 4:
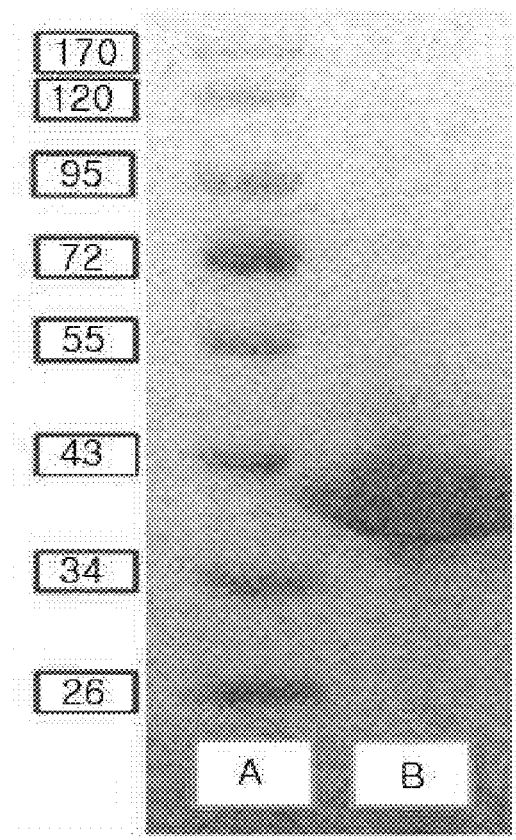
FIG. 4 shows agarase which was expressed in E. coli and was purified; 12% SDS-polyacrylamide gel electrophoresis; Lane A represents a molecular size marker, and B: represents α-neoagarobiose hydrolase.

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

As used herein, "a" or "an" may mean one or more than one of an item unless otherwise defined.

The term "recombination," as used in connection with a cell, a nucleic acid, a protein or a vector, means that the cell, nucleic acid, protein or vector is modified by introduction of a heterogenous nucleic acid or protein or a change in innate nucleic acid or protein, or the cell is derived from such a modified cell. That is, for example, a recombination cell expresses a gene that has not been found in an innate (non-recombinant) form of the cell, or otherwise expresses an innate gene that is abnormally expressed or is not expressed at all.

The terms "protein" and "polypeptide" may be interchangeably used herein. In the present invention, a conventional one-letter code or three-letter code is used for amino acid residues.

The term "gene" refers to upstream and downstream regions of a coding region of the enzyme of the present invention, as well as DNA fragments associated with production of a polypeptide, including sequences interposed between respective coding fragments.

The term "nucleic acid" encompasses single-stranded or double-stranded DNA, RNA, and chemical variants thereof. The term "nucleic acid" and "polynucleotide" may be interchangeably used herein. Since the degeneracy may occur in the genetic codes, at least one codon may be used to encode a certain amino acid, and the present invention encompasses polynucleotides encoding any amino acid sequences.

The term "vector" refers to a polynucleotide sequence designed to introduce a nucleic acid sequence into at least one cell type. Examples of the vector include a cloning vector, an expression vector, a shuttle vector, plasmid, phage particle, cassette and the like.

The term "expression vector" used herein refers to a DNA construct having a DNA sequence operatively connected to a suitable control sequence to express target DNA in a suitable host. These control sequences may include a promoter initiating transcription, any operator sequences controlling transcription, a sequence encoding a suitable ribosomal binding site on mRNA, an enhancer and a sequence controlling initiation and termination of the transcription.

The term "promoter" means a regulatory sequence associated with linkage of RNA polymerase so as to initiate the transcription of a gene. The promoter may be an inducible promoter or constitutive promoter.

The term "derived" includes the terms "originating from," "obtained from" or "obtainable from" and "isolated from." When the term is used herein, it means that a polypeptide encoded by the nucleotide sequence is produced in a cell in which the nucleotide is innately present or the nucleotide sequence is inserted.

The term "culture," "culturing," "cultivation" or "cultivating" means that a microorganism cell colony is grown in a liquid or solid medium under suitable conditions. According to one preferred embodiment, the culturing or cultivating means a biological conversion of a substrate including agarose into a final product (typically in a container or reactor). The "fermentation" or "fermenting" means that an organic material is enzymatically and anaerobically degraded by a microorganism to produce simpler organic compounds. The fermentation generally occurs under the anaerobic conditions, but may also occur at the presence of oxygen. Therefore, the term is not intended to be limited to the strict anaerobic conditions.

The terms "recovering" or "recovery," "isolating" or "isolation" and "separating" or "separation" used herein mean that a compound, a protein, a cell, a nucleic acid or an amino acid is removed from at least one component which is spontaneously bound thereto.

The terms "transforming" or "transformation," "stably transforming" or "stable transformation" and "gene-transplanting" or "gene transplantation" used in connection with a cell used herein mean that a cell has a non-innate (for example, heterogenous) nucleic acid sequence which is present as an episome plasmid maintained through several generations, or is integrated into a genome of the cell.

The term "expression" or "expressing" used herein means a method of producing a polypeptide based on the nucleic acid sequence of a gene. Such a method includes transcription and translation.

The term "introduction" or "introducing" used when a nucleic acid sequence is inserted into a cell means "transfecting" or "transfection," "transforming" or "transformation," or "transducing" or "transduction," and includes integrations of a nucleic acid sequence into eukaryote or prokaryote. In this case, the nucleic acid sequence is integrated into the genome (for example, chromosome, plasmid, chromatophore, or mitochondrial DNA) of a cell, and converted into an autonomous replicon, or temporarily expressed.

1. Enzymatic Process for Production of Fermentable Sugar, D-Galactose, from α-Neoagarobiose During Pretreatment Process of Marine Biomass Including Red Algae Two pretreatment methods, for example, a chemical method and an enzymatic method, may be used to produce fermentable sugars from agar polysaccharide. First, the chemical method has a problem in that since complex polysaccharides are randomly degraded, it is difficult to selectively produce desired fermentable monosaccharides, and it may also generate by-products which inhibit the fermentation of the produced sugars. In addition, since a significant amount of a contaminant is discharged during the alkali treatment or acid treatment, lots of costs may incur to clean up the contaminant. Therefore, the chemical method is not suitable for the method for producing fermentable sugars which may be used by microorganisms. An enzyme which may be used in such an enzymatic method includes α-agarase or β-agarase. As the enzyme degrading the agar polysaccharide, α-agarase serves to finally produce γ-agarobiose disaccharides by hydrolyzing α-linkages among α-1,3 and β-1,4 linkages present in the agar polysaccharide, and β-agarase serves to produce α-neoagarobiose disaccharides by cleaving β-linkages. When the β-agarase is used during such an enzymatic pretreatment process, the final product is α-neoagarobiose, which is a non-fermentable sugar which may not be used by conventional microorganisms. In order to perform a pretreatment process of finally converting the α-neoagarobiose into fermentable sugars, α-neoagarobiose hydrolase is necessarily required.

2. Production of Galactose or AHG from α-Neoagarobiose which is an Enzymatic Degradation Product of Agar Polysaccharide 3,6-Anhydro-L-galactose (AHG) obtained by hydrolysis of α-neoagarobiose are not currently commercially available, and only D-AHG may be purchased. However, the D-AHG is very expensive (200 pounds (G.B.)/100 mg as of 2009, Dextra Laboratories). Therefore, it is possible to mass-produce expensive AHG from agarose using the enzyme of the present invention.

The present inventors have found that an ocean bacterium, *S. degradans*, has an α-neoagarobiose hydrolase activity, and screened a corresponding gene for the first time. Also, *Escherichia coli* (*E. coli*) was transformed to mass-produce a protein, from which the α-neoagarobiose hydrolase activity was confirmed. The enzymatic activity of a novel α-neoagarobiose hydrolase gene was used to apply to pretreatment of an ocean biomass including the agar polysaccharide, and used to obtain fermentable sugars including galactose from α-neoagarobiose obtained by the pretreatment process.

In recent years, an ocean bacterium, *S. degradans*, which can grow using the agar polysaccharide as a carbon source was found, and its genomic sequence was currently determined.

In order to screen a gene of the α-neoagarobiose hydrolase, the activity of α-neoagarobiose hydrolase was first confirmed in *S. degradans*. Next, the presence of an α-neoagarobiose hydrolase gene (protein database Uniprot database ID: Q21HB2) belonging to the glycosyl hydrolase family 32 among genes of *S. degradans* was estimated through the genomic sequence information analysis. In order to confirm whether a protein actually has an α-neoagarobiose hydrolase activity, a gene coding for the protein was cloned into an expression vector, and the protein was expressed in *E. coli*, separated and purified to finally confirm the activity of the enzyme.

EXAMPLES

Hereinafter, preferred embodiments of the present invention will be described in detail referring to the accompanying drawings. Prior to the description, it should be understood that the terms used in the specification and appended claims should not be construed as limited to general and dictionary meanings, but interpreted based on the meanings and concepts corresponding to technical aspects of the present invention on the basis of the principle that the inventor is allowed to define terms appropriately for the best explanation. Therefore, the description proposed herein is just a preferable example for the purpose of illustrations only, not intended to limit the scope of the invention, so it should be understood that other equivalents and modifications could be made thereto without departing from the scope of the invention.

Example 1

Confirmation of Enzymatic Activity of α-Neoagarobiose Hydrolase from a Crude Extract of *S. degradans*

In order to confirm whether or not *S. degradans* has an enzyme activity to produce monosaccharides, galactose and AHG, through hydrolysis by α-neoagarobiose, a crude extract was obtained to assay the enzyme activity using the following method. When *S. degradans* was grown to mid-log phase in a medium containing seawater, 40 ml of a culture solution was centrifuged, and cells were disrupted using ultrasonication, then a crude extract was obtained, Agar polysaccharide was degraded with β-agarase to obtain product. The product which was degraded with β-agarase was used as a substrate to observe a reaction/degradation product through TLC. Lane A represents a galactose standard, Lane B represents a reaction product obtained by reaction of 0.25% (w/v) agarose with an endogenous crude enzyme solution of *S. degradans*, and Lane C represents a reaction product analyzed through TLC after the reaction of 0.3% (w/v) red seaweed, dry agar-agar powder, with an endogenous crude enzyme solution of *S. degradans*. From the reaction with the endogenous crude enzyme solution of *S. degradans*, it was seen that monosaccharides (for example AHG and galactose) and disaccharides were produced from both of the agarose and the agar-agar powder. Accordingly, it was revealed that *S. degradans* had enzymes to produce the monosaccharides such as galactose and AHG through the endogenous hydrolysis of α-neoagarobiose.

According to the present invention, a base sequence of the screened gene and an amino acid sequence of the corresponding protein are shown in FIG. 3.

Example 2

Biochemical Activity and Characterization of α-Neoagarobiose Hydrolase

Figure 5:
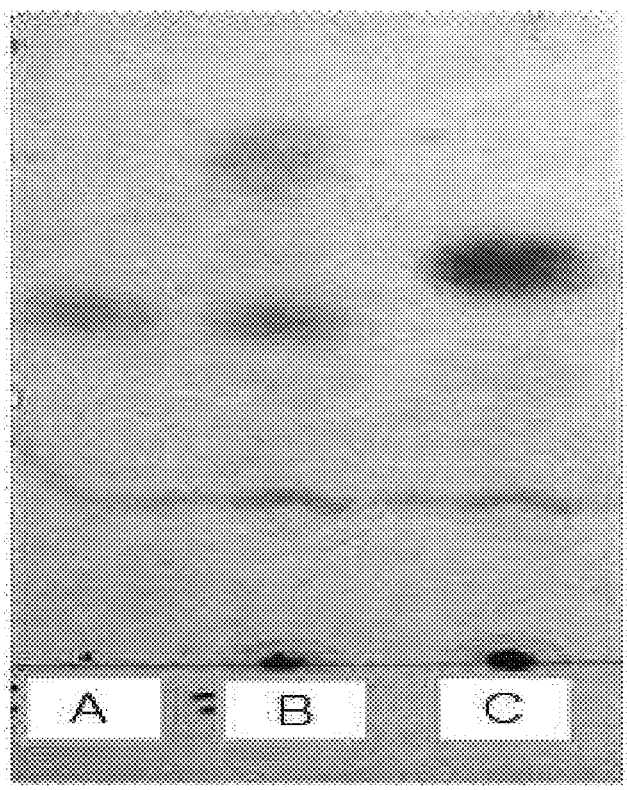
FIG. 5 is a TLC photograph showing reaction products which were produced from hydrolysis of agarose by α-neoagarobiose hydrolase and β-agarase. An enzymatic reaction was performed at 30° C. in 20 mM Tris-HCl (pH6.8), and a concentration of a substrate was 0.25% (w/v). (A): galactose, and (B and C): reaction mixtures. A: galactose standard; B: reaction product of α-neoagarobiose hydrolase (2-hour reaction); and C: neoagarobiose.

The activity of purified α-neoagarobiose hydrolase was confirmed, as follows. First, an agar polysaccharide was treated with β-agarase to produce neoagarobiose as a final product of the enzymatic treatment. Then, the neoagarobiose was used as a substrate to confirm that it is a reaction product of the α-neoagarobiose hydrolase using TLC (TLC results shown in FIG. 5). It was confirmed that the substrate treated with the α-neoagarobiose hydrolase under the TLC solvent condition (n-buthanol:EtOH:water=3:2:2) was degraded into materials which are expected to be galactose and AHG. From the TLC results, it was revealed that a Rf value of galactose was approximately 0.46, and a Rf value of neoagarobiose was approximately 0.58.

Figure 6:
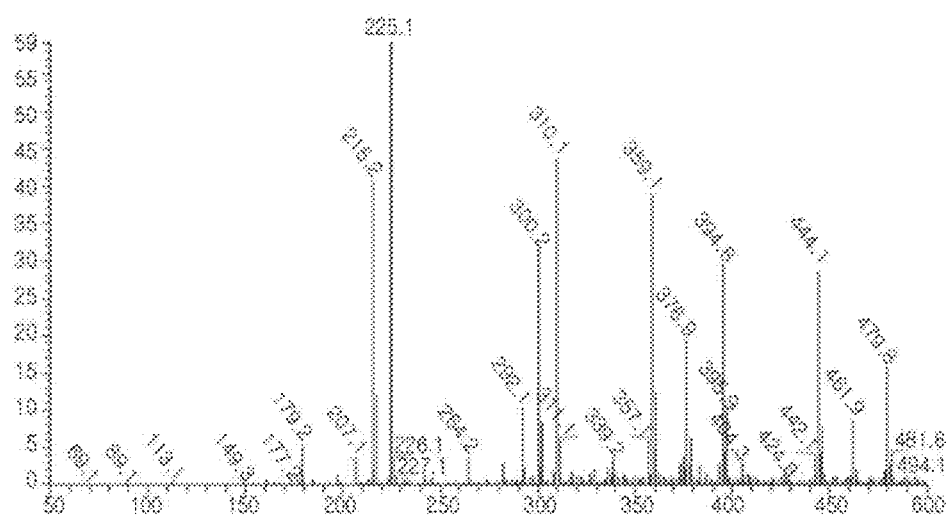
FIG. 6 shows reaction products which were produced from hydrolysis of agarose by α-neoagarobiose hydrolase and β-agarase being confirmed through liquid chromatography-mass spectrometry. From the mass spectrometric results of the reaction products using a mass spectrometer (Negatively inionized into formate (HCOO—, molecular weight: 45)), it was confirmed that a molecular weight of galactose was 225.1 (180+45), and a molecular weight of AHG was 207.1 (162+45), as shown in FIG. 6. Therefore, it was revealed that the reaction products of the α-neoagarobiose hydrolase were galactose and AHG. That is, the results obtained through mass spectrometry by the Seoul branch of the Korea Basic Science Institute were obtained from the mass spectrometric spectra as shown in FIG. 6, and we confirmed the hydrolysis products by the enzyme as a result of analysis of the results.

In order to measure molecular weights of products obtained by the hydrolysis of the α-neoagarobiose hydrolase, the molecular weights of the products were determined through the liquid chromatography-mass spectrometry (LC-MS). The LC-MS results showed that the AHG has a molecular weight of 162, and the galactose has a molecular weight of 180. From the LC-MS results, it was seen that 207.1 m/z corresponds to a molecular weight of the AHG bound to formic acid, which indicates the presence of the AHG, and 179.1 m/z and 225.1 m/z correspond to molecular weights of the galactose and the galactose bound to formic acid, respectively, which indicates the presence of the galactose. Therefore, as shown through the LC-MS, it was confirmed that two monosaccharides, galactose and AHG, were the reaction products of the neoagarobiose hydrolase (see FIG. 6).

Example 3

α-Neoagarobiose Hydrolase-Specific Peptide Motif Sequence

In general, a protein motif refers to a short peptide sequence which appears like a kind of a pattern in proteins having the same molecular functions. Such a protein motif is evolutionarily highly conserved in the entire protein sequence, and is represented by a patterned amino acid sequence represented by a domain which is representative of the molecular functions and has an active region (Sigrist C. J. A., Cerutti L., Hulo N., Gattiker A., Falquet L., Pagni M., Bairoch A., Bucher P. PROSITE: a documented database using patterns and profiles as motif descriptors. Brief Bioinform. 3:265-274 (2002); Sigrist C. J. A., De Castro E., Langendijk-Genevaux P. S., Le Saux V., Bairoch A., Hulo N. ProRule: a new database containing functional and structural information on PROSITE profiles. Bioinformatics. 2005 Nov. 1; 21(21):4060-6. Epub 2005 Aug. 9; Timothy L. Bailey, Nadya Williams, Chris Misleh, and Wilfred W. Li, MEME:

discovering and analyzing DNA and protein sequence motifs, Nucleic Acids Research, Vol. 34, pp. W369-W373, 2006).

Figure 7B:
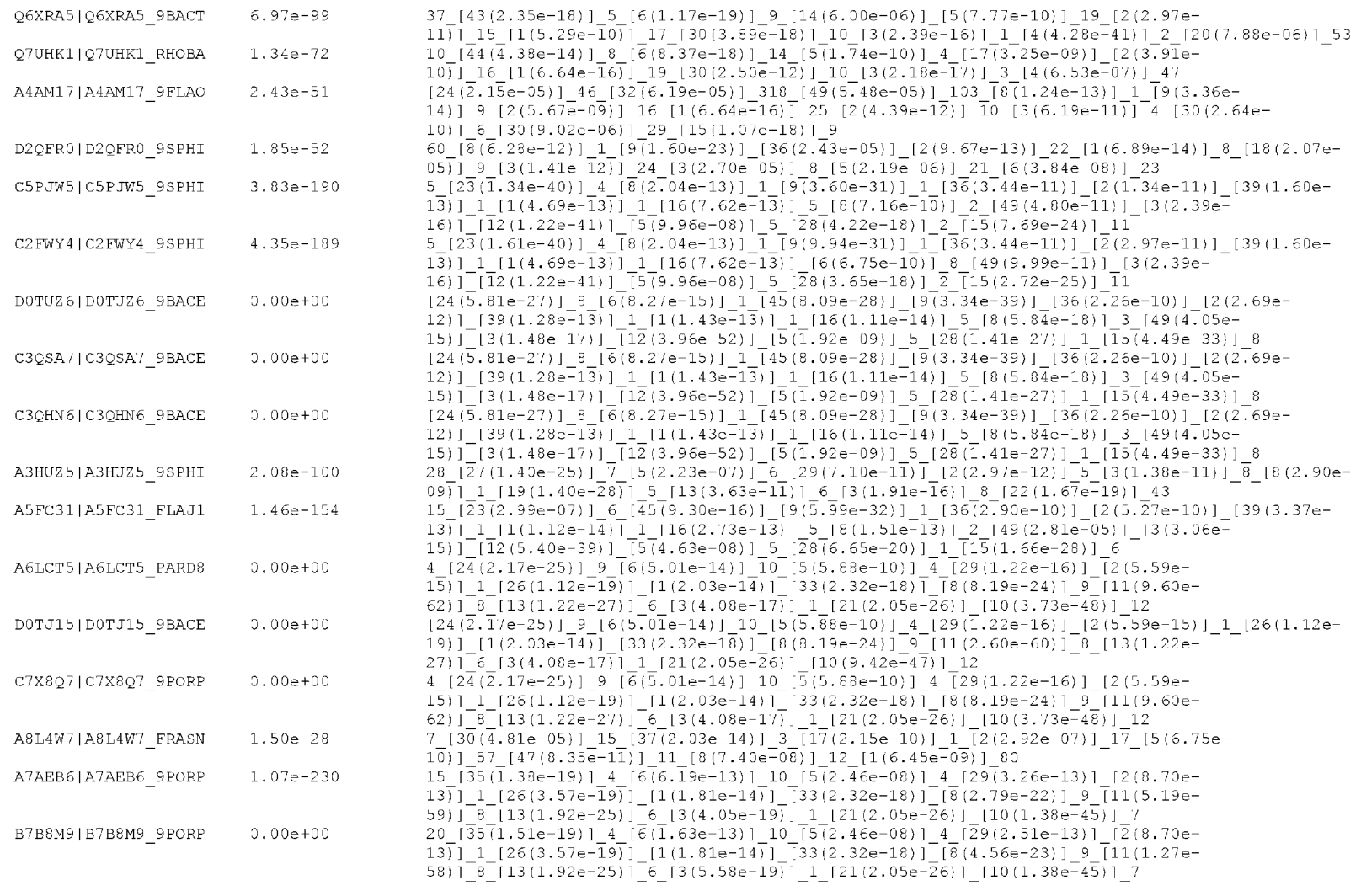
Figure 7C:
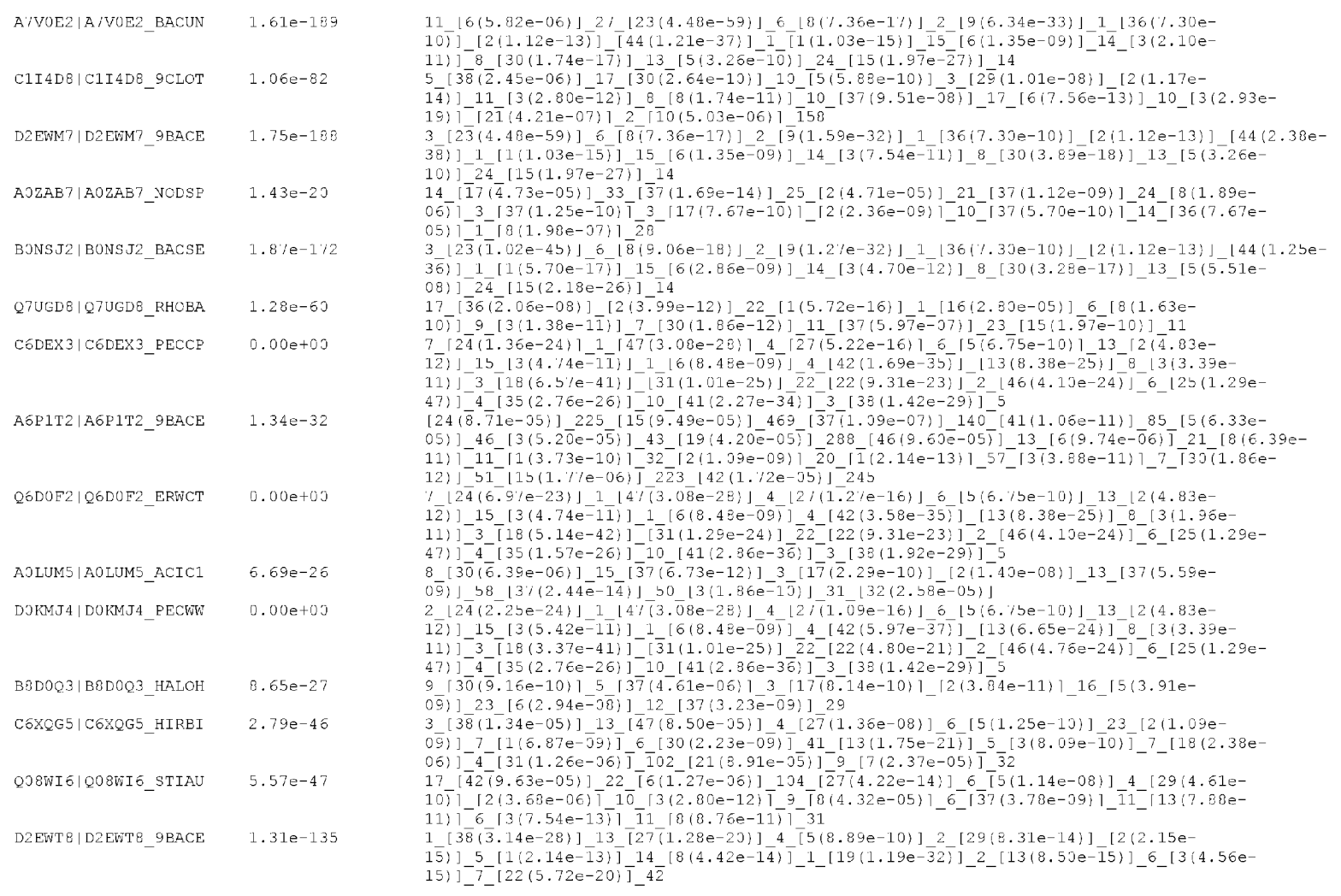

In order to confirm a sequence of the protein motif which can define the α-neoagarobiose hydrolase, first, an amino acid sequence of the α-neoagarobiose hydrolase was used as a template, and public database was searched through NCBI blast to collect 60 proteins (including α-neoagarobiose hydrolase) having a statistical significance (E-value <0.001). Theses sequences were used to search motifs specific to the α-neoagarobiose hydrolase using a protein motif search program, MEME; See the World Wide Web (www) at meme.sdsc.edu/meme4_1/intro.html; used parameter: mode=zero or one occurrence & nsites=50, mwin=8, and the other conditions uses default parameters; Timothy L. Bailey, Nadya Williams, Chris Misleh, and Wilfred W. Li, MEME: discovering and analyzing DNA and protein sequence motifs, Nucleic Acids Research, Vol. 34, pp. W369-W373, 2006). As a result, it was confirmed that the α-neoagarobiose hydrolase of *S. degradans* as shown in FIG. 7 has 13 specific motifs (motifs 1, 2, 3, 4, 5, 6, 7, 14, 16, 17, 20, 34 and 40) among the total 50 motifs obtained through analysis of the proteins having homologies. Therefore, it was able to confirm that the 13 specific motifs were representative of the activities of the α-neoagarobiose hydrolase. Among them, motifs 7 and 34 are two essential motifs which are inevitably present in the proteins representative of the α-neoagarobiose hydrolase activity, and shown in FIGS. 8 and 9, respectively (The protein motifs are generally represented according to a regular expression, and expressed in the same manner as in the drawings; Sigrist C. J. A., Cerutti L., Hulo N., Gattiker A., Falquet L., Pagni M., Bairoch A., Bucher P. PROSITE: a documented database using patterns and profiles as motif descriptors. Brief Bioinform. 3:265-274(2002)). Therefore, the proteins including some of the 13 specific motifs and inevitably including motifs 7 and 34 among the 13 specific motifs may have the α-neoagarobiose hydrolase activity (See FIG. 8). Among the proteins having a sequence homology with the α-neoagarobiose hydrolase, we confirmed 10 proteins including some of the 13 specific motifs and inevitably including motifs 7 and 34 (See FIGS. 9 and 10).

The 10 proteins, which include some of the 13 specific motifs previously found in the α-neoagarobiose hydrolase and inevitably include motifs 7 and 34, have been found on the public database. The origins of the proteins were derived respectively from *P. atlantica* T6c, *Microscilla* sp. PRE1, *Bacteroides plebeius* DSM 17135, *Gramella forsetii* (strain KT0803), *Flavobacteriales bacterium* HTCC2170, *Paenibacillus* sp. oral taxon 786 str. D14, and *Ruminococcus* sp. 5_1_39BFAA, *S. coelicolor* A3. Their respective amino acid sequences are shown in FIG. 10.

Figure 11:
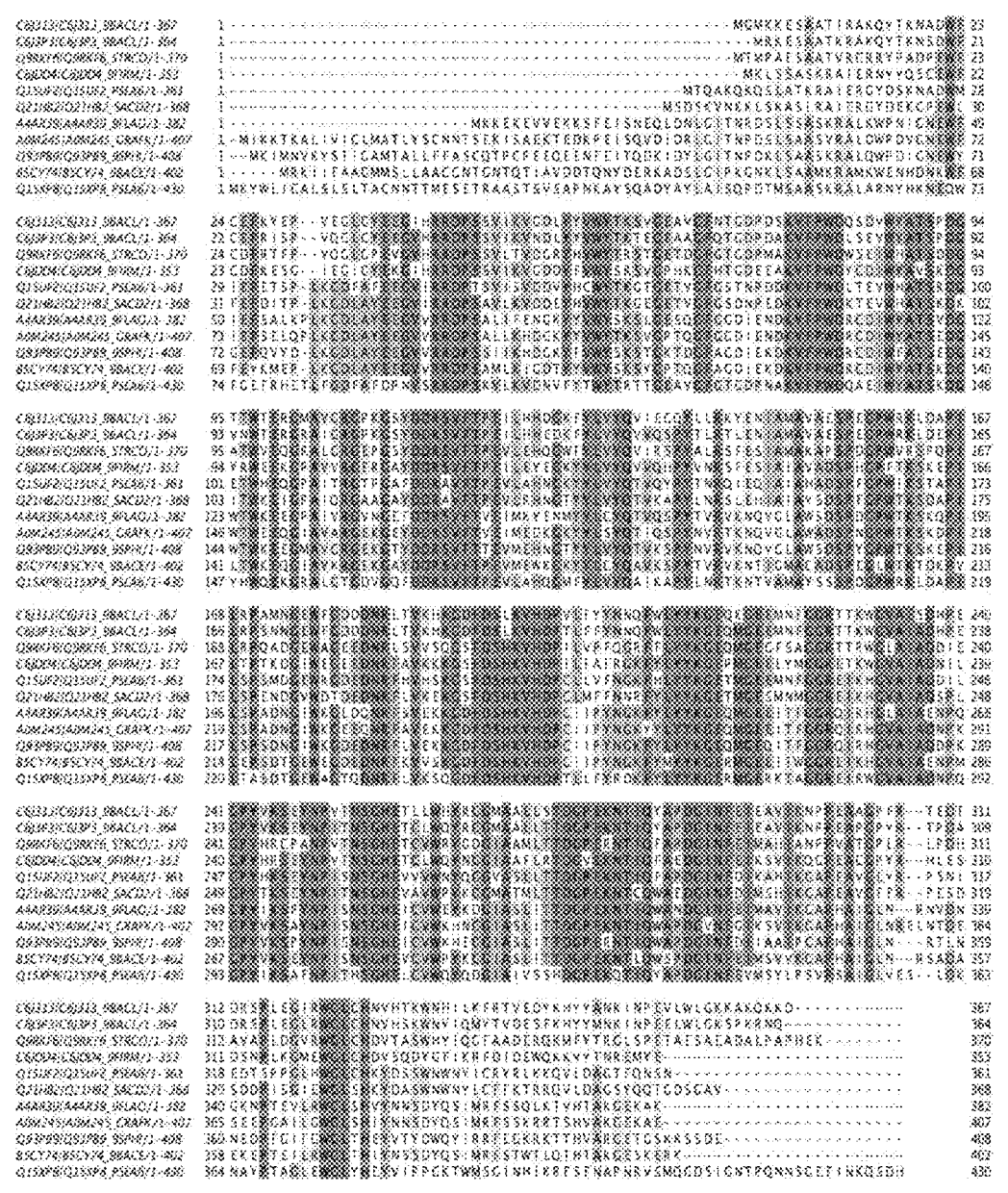

After the ten proteins including some of the 13 specific motifs and inevitably including motifs 7 and 34 were selected from the proteins having a sequence homology with the α-neoagarobiose hydrolase as described above, their sequences as shown in FIG. 11 were listed in a multiple alignment manner. The sequences of the 10 proteins are shown in FIGS. 9 and 10.

Example 4

Confirmation of Protein Sequence Homology of α-Neoagarobiose Hydrolase Gene

Candidate genes, which are expected to have similar functions, were screened through the sequence homology search for the proteins of the *S. degradans*-derived hydrolases. The specific functions of the candidate genes were unknown in the art, but it was known that all the candidate genes belong to the glycoside hydrolase family 32 (GH32) according to the carbohydrate-related enzyme/protein database, CAZy See, the World Wide Web (www) at cazy.org. The known functions of the proteins belonging to the GH32 family include functions of enzymes, such as invertase (EC 3.2.1.26); endo-inulinase (EC 3.2.1.7); β-2,6-fructan 6-levanbiohydrolase (EC 3.2.1.64); endo-levanase (EC 3.2.1.65); exo-inulinase (EC 3.2.1.80); fructan β-(2,1)-fructosidase/1-exohydrolase (EC 3.2.1.153); fructan β-(2,6)-fructosidase/6-exohydrolase (EC 3.2.1.154); sucrose: sucrose 1-fructosyltransferase (EC 2.4.1.99); fructan:fructan 1-fructosyltransferase (EC2.4.1.100); sucrose:fructan 6-fructosyltransferase (EC 2.4.1.10); fructan:fructan 6G-fructosyltransferase (EC 2.4.1.243); and levan fructosyltransferase (EC 2.4.1.-). Therefore, it is disclosed in the present invention for the first time that some of the proteins belonging to the GH32 family have the same molecular function as the α-neoagarobiose hydrolase activity.

Among sequences screened from the homology search for the amino acid sequences of *S. degradans* 2-40-derived α-neoagarobiose hydrolases (hereinafter, referred to as "α-NABH"), protein sequences having at least 50% homology are listed according to the E-value from the blast search, as follows (Uniprot database numbers are described below, and original microorganisms and % identities are expressed in the parentheses).

1. Q15UF2 (*P. atlantica* (strain T6c/BAA-1087), 70%),
2. Q93PB3 (*Microscilla* sp. PRE1., 59%),
3. B4CY74 (*Bacteroides plebeius* DSM17135., 60%),
4. A0M245 (*Gramella forsetii* (strainKT0803)., 56%),
5. A4AR39 (*Flavobacteriales bacterium* HTCC2170., 57%),
6. C6J3P3 (*Paenibacillus* sp. oral taxon 786 str. D14., 58%),
7. C6JDD4 (*Ruminococcus* sp. 5_1_39BFAA., 58%),
8. C6J313 (*Paenibacillus* sp. oral taxon 786 str. D14., 57%),
9. Q15XP8 (*P. atlantica* (strainT6c/BAA-1087), 55%),
10. Q9RKF6 (*S. coelicolor*, 56%)

Example 5

Confirmation of Expression and Size in *E. coli*

Among the previously screened proteins having at least 50% sequence homology, the *P. atlantica* T6c-derived protein (Q15UF2) having the highest sequence homology, and the *S. coelicolor* A3-derived protein (Q9RKF6) having the lowest sequence homology were cloned, respectively, to confirm whether or not the cloned proteins have α-NABH activity. First, base sequences of genes coding for these proteins were inserted respectively to an *E. coli* expression vector (pET21a, Novagen, U.S.) (hereinafter, an expression vector including the *P. atlantica* T6c-derived α-NABH gene was named "pPsAGAJ," and an expression vector including the *S. coelicolor* A3-derived α-NABH gene was named "pScAGAJ"). In order to confirm whether the recombinant α-NABH is successfully expressed in *E. coli*, the expression vectors, pPsA-GAJ and pScAGAJ, were transformed into *E. coli* BL21 (DE3) used to express a target protein, and the transformants were plated on a solid medium supplemented with a 50 mg/L concentration of antibiotic ampicillin. A colony obtained through the above-described transformation was seeded in a Luria-Bertani (LB) medium supplemented with a 50 mg/L concentration of antibiotic ampicillin, and incubated at 37° C. for a day while stirring to obtain cells. In order to confirm the expression of the α-NABH gene, the transformants were then seeded in a LB medium supplemented with a 50 mg/L concentration of antibiotic ampicillin, and incubated at 37° C. while stirring until an $OD_{600}$ value reached 0.5 to 1.0. A 0.5 mM/L concentration of IPTG was added to the LB medium to induce the expression of the α-NABH gene while stirring at 180 rpm for 4 hours. The resultant culture solution was centrifuged (at 12,000 rpm and 4° C. for 10 minutes) to recover cells. The recovered cell was then suspended in a 20 mM Tris buffer (Tris-HCl, pH 7.4), and disrupted using ultrasonication. Then, the size of the target protein was confirmed through 12% SDS-PAGE. The disrupted suspension in which the size of the target protein was confirmed was centrifuged for 15 minutes to obtain a supernatant, which was then used as a crude enzyme solution.

Example 6

Confirmation of Biochemical Activity of α-Neoagarobiose Hydrolase

The activity of purified α-NABH was confirmed, as follows. First, agar polysaccharide was treated with β-agarase to produce neoagarobiose which is a final product of the enzymatic treatment, and the neoagarobiose was then used as a substrate to confirm the presence of a reaction product of α-NABH using TLC. The confirmation through the TLC was performed by dropping 1 ul of a reaction solution on a silica gel 60 TLC plate and developing the silica gel 60 TLC plate under a TLC solvent condition (n-buthanol:EtOH:water=3:2:2). The developed TLC plate was treated with sulphuric acid (10% (v/v) $H_2SO_4$ in ethanol) that is a primary treatment solution, and dried. Then, the primarily treated plate was treated with naphthoresorcinol (0.2% (w/v) naphthoresorcinol in ethanol) that is a secondary treatment solution. The resultant TLC plate was dried, and heated.

The results from Example 4 to 6 are listed, as follows.

Figure 12:
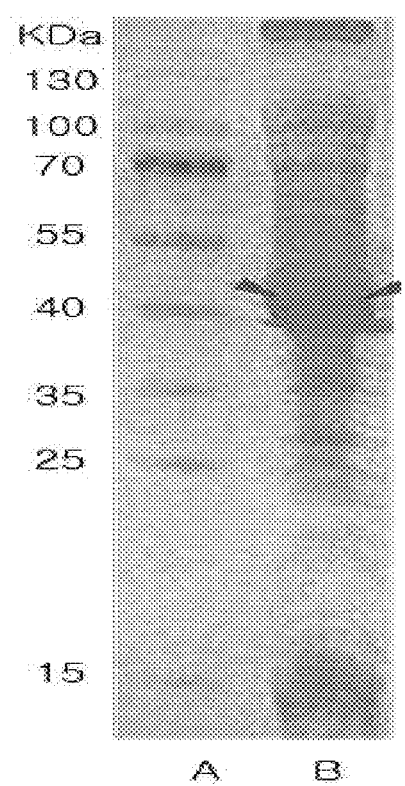
FIG. 12 shows *Pseudoalteromonas atlantica (P. atlantica)*-derived agarase which was expressed in *E. coli* and was purified; 12% SDS-polyacrylamide gel electrophoresis; Lane A represents a molecular size marker; and Lane B represents α-neoagarobiose hydrolase.
Figure 13:
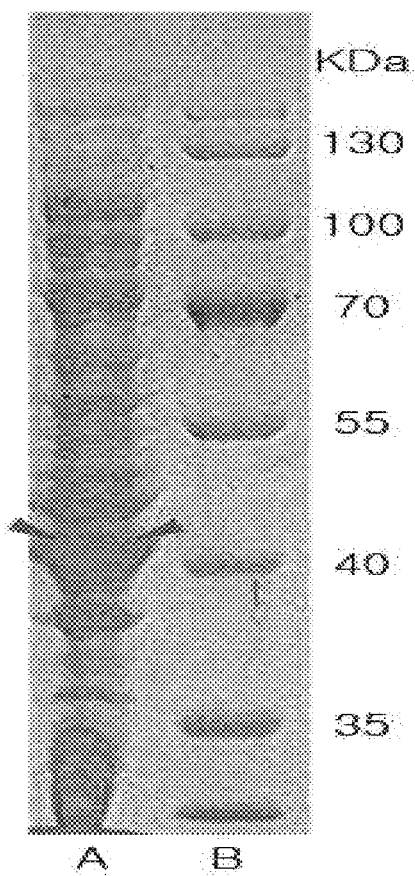
FIG. 13 shows *Streptomyces coelicolor (S. coelicolor)*-derived agarase which was expressed in *E. coli* and was purified; 12% SDS-polyacrylamide gel electrophoresis; Lane A represents α-neoagarobiose hydrolase; and Lane B represents a molecular size marker.

The expression and size of the *P. atlantica-* and *S, coelicolor*-derived α-NABH with which an expression strain, *E. coli* BL21(DE3), was transformed was confirmed through 12% SDS-PAGE. Expected molecular weights of the *P. atlantica-* and *S, coelicolor*-derived α-NABH were approximately 40.7 kDa and 41.1 kDa, respectively, which were confirmed to correspond to expected molecular weights (FIG. 12, FIG. 13).

Figure 14:
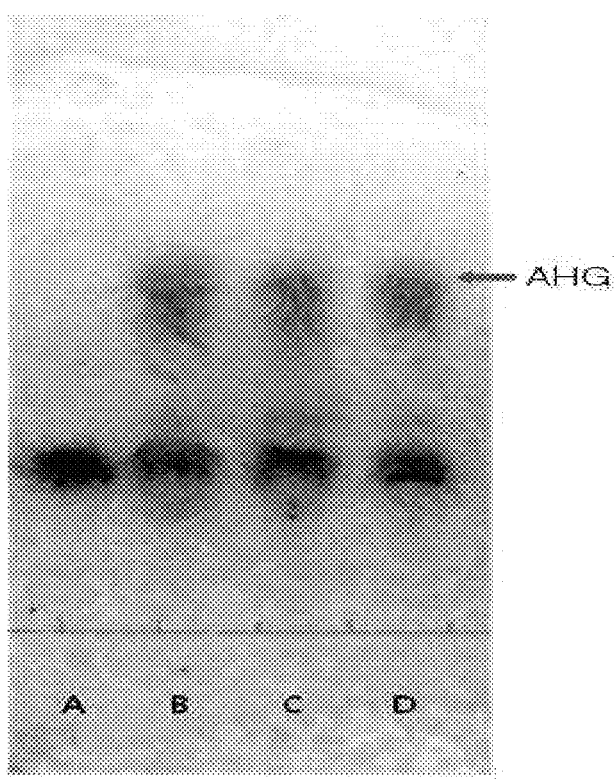
FIG. 14 is a TLC photograph showing reaction products produced from hydrolysis of agarose by α-neoagarobiose hydrolase and β-agarase. An enzymatic reaction was performed at 30° C. in 20 mM Tris-HCl (pH6.8) for 2 hours, and a concentration of a substrate was 0.25% (w/v). (A): galactose, and (B to D): reaction mixtures. Lane A: galactose standard; Lane B: reaction product of S. degradans 2-40-derived α-neoagarobiose hydrolase; Lane C: reaction product of P. atlantica T6c-derived α-neoagarobiose hydrolase; and Lane D: reaction product of S. coelicolor A3-derived α-neoagarobiose hydrolase.

Also, D-galactose was used as a reference material to confirm the presence of an expected degradation product. The α-NABH-treated disaccharide, neoagarobiose, was confirmed to be degraded into expected materials such as galactose and AHG whose Rf value is confirmed to be the same as that of D-galactose (FIG. 14).

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. A method for preparing galactose 3,6-anhydro-L-galactose (AHG), comprising steps of:

obtaining an α-neoagarobiose hydrolase from a culture of host cells transformed with a recombinant vector, wherein the recombinant vector comprises an isolated nucleic acid molecule encoding a protein comprising the amino acid sequence set forth in SEQ ID NO: 2;

combining an α-neoagarobiose, a buffer and the α-neoagarobiose hydrolase to form a reaction solution;

heating the reaction solution at a temperature effective to cause a reaction between the α neoagarobiose and the α-neoagarobiose hydrolase and obtaining galactose or AHG from the degradation product.

* * * * *

SEQUENCE LISTING

```
<160> NUMBER OF SEQ ID NOS: 25

<210> SEQ ID NO 1
<211> LENGTH: 361
<212> TYPE: PRT
<213> ORGANISM: Pseudoalteromonas atlantica T6c

<400> SEQUENCE: 1

Met Thr Gln Ala Lys Gln Lys Gln Ser Leu Ala Thr Lys Arg Ala Ile
1               5                   10                  15

Glu Arg Gly Tyr Asp Ser Lys Asn Ala Asp Trp Met Ile Glu Phe Glu
            20                  25                  30

Thr Ser Pro Leu Lys Gly Asp Phe Ala Phe Glu Glu Gly Val Ile Arg
        35                  40                  45

Arg Asp Pro Thr Ser Val Ile Ser Val Asp Asp Val Tyr His Cys Trp
    50                  55                  60

Tyr Thr Lys Gly Thr Gly Glu Thr Val Gly Phe Gly Ser Thr Asn Pro
65                  70                  75                  80

Asp Asp Lys Val Phe Pro Trp Asp Leu Thr Glu Val Trp His Ala Thr
                85                  90                  95

Ser Arg Asp Gly Glu Thr Trp His Glu Gln Gly Pro Ala Ile Thr Arg
            100                 105                 110

Gly Thr Pro Gly Ala Phe Asp Asp Arg Ala Val Phe Thr Pro Glu Val
        115                 120                 125

Leu Ala His Asn Gly Lys Tyr Tyr Leu Val Tyr Gln Thr Val Gln Tyr
    130                 135                 140

Pro Tyr Thr Asn Arg Gln Ile Glu Gln Ile Ala Ile Ala His Ala Asp
145                 150                 155                 160

Ser Pro Phe Gly Pro Trp Ile Lys Ser Thr Ala Pro Ile Leu Ser Pro
                165                 170                 175
```

```
Ser Met Asp Gly Glu Trp Arg Gly Asp Glu Asp Asn Arg Phe His Val
            180                 185                 190

His Ser Lys Gly Ser Phe Asp Ser His Lys Val His Asp Pro Cys Leu
        195                 200                 205

Leu Val Phe Asn Gly Lys Phe His Leu Tyr Tyr Lys Gly Glu Thr Met
    210                 215                 220

Gly Glu Glu Met Asn Phe Gly Arg Glu Ile Lys His Gly Val Ala
225                 230                 235                 240

Ile Ala Asp Asp Ile Leu Gly Pro Tyr His Lys Ser Glu Tyr Asn Pro
                245                 250                 255

Ile Ser Asn Ser Gly His Glu Val Val Trp Asn Tyr Gln Gly Gly
            260                 265                 270

Val Ala Ser Leu Leu Thr Thr Asp Gly Pro Glu Lys Asn Thr Ile Gln
        275                 280                 285

Phe Ala Pro Asp Gly Ile Asn Phe Asp Ile Lys Ala His Ile Lys Gly
    290                 295                 300

Ala Pro Glu Ala Val Gly Leu Tyr Arg Pro Ser Asn Ile Glu Asp Thr
305                 310                 315                 320

Ser Pro Pro Gly Leu His Trp Gly Leu Cys His Lys Tyr Asp Ser Ser
                325                 330                 335

Trp Asn Trp Asn Tyr Ile Cys Arg Tyr Arg Leu Lys Lys Gln Val Leu
            340                 345                 350

Asp Ala Gly Thr Phe Gln Asn Ser Asn
        355                 360

<210> SEQ ID NO 2
<211> LENGTH: 370
<212> TYPE: PRT
<213> ORGANISM: Streptomyces coelicolor A3

<400> SEQUENCE: 2

Met Thr Met Pro Ala Glu Ser Ala Ala Thr Val Arg Gly Arg Arg Tyr
1               5                   10                  15

Pro Ala Asp Pro Glu Trp Phe Cys Asp Phe Arg Thr Phe Pro Val Gln
            20                  25                  30

Gly Leu Gly Pro Glu Val Gly Val His Arg Arg Asp Pro Ser Ser Val
        35                  40                  45

Leu Thr Val Asp Gly Arg Tyr His Val Trp Tyr Thr Arg Ser Thr Gly
    50                  55                  60

Glu Thr Asp Gly Phe Gly Thr Gly Asp Pro Met Ala Lys Val Phe Pro
65                  70                  75                  80

Trp Asp Trp Ser Glu Ile Trp His Ala Thr Ser Asp Asp Gly Ala Thr
                85                  90                  95

Trp Val Glu Gln Gly Arg Ala Leu Gly Arg Gly Glu Pro Gly Ser Tyr
            100                 105                 110

Asp Asp Arg Ser Val Phe Thr Pro Glu Val Leu Glu His Gln Gly Trp
        115                 120                 125

Phe Tyr Leu Val Tyr Gln Val Ile Arg Ser Pro Tyr Ala Leu Arg Ser
    130                 135                 140

Phe Glu Ser Ile Ala Met Ala Lys Ala Pro Ser Pro Asp Gly Pro Trp
145                 150                 155                 160

Val Arg Ser Pro Gln Pro Ile Leu Arg Pro Gln Ala Asp Gly Glu Trp
                165                 170                 175

Ala Gly Glu Glu Asp Asn Arg Leu Ser Val Val Ser Gln Gly Ser Phe
```

```
            180                 185                 190
Asp Ser His Lys Val His Asp Pro Ile Leu Val Pro Phe Gln Gly Arg
        195                 200                 205

Phe Phe Leu Tyr Tyr Lys Gly Glu Gln Met Gly Glu Gly Phe Ser Ala
    210                 215                 220

Gly Gly Arg Thr Thr Arg Trp Gly Leu Ala Ile Ala Asp Asp Ile Glu
225                 230                 235                 240

Gly Pro Tyr His Arg Cys Pro Ala Asn Pro Val Thr Asn Ser Gly His
                245                 250                 255

Glu Thr Cys Val Trp Arg Tyr Gly Asp Gly Ile Ala Ala Met Leu Thr
            260                 265                 270

Thr Asp Gly Pro Glu Arg Asn Thr Ile Gln Phe Ala Pro Asp Gly Ile
        275                 280                 285

Asn Phe Glu Ile Met Ala His Ile Ala Asn Pro Val Ala Thr Gly
    290                 295                 300

Pro Leu Arg Leu Pro Asp His Ala Val Ala Pro Leu Asp Gly Val Arg
305                 310                 315                 320

Trp Gly Leu Cys His Asp Val Thr Ala Ser Trp His Tyr Ile Gln Gly
                325                 330                 335

Phe Ala Ala Asp Glu Arg Gln Lys Met Phe Tyr Thr Arg Gly Leu Ser
            340                 345                 350

Pro Glu Thr Ala Glu Ser Ala Glu Ala Asp Ala Leu Pro Ala Pro His
        355                 360                 365

Glu Lys
    370

<210> SEQ ID NO 3
<211> LENGTH: 407
<212> TYPE: PRT
<213> ORGANISM: Gramella forsetii (strain KT0803)

<400> SEQUENCE: 3

Met Ile Lys Lys Thr Lys Ala Leu Ile Val Ile Gly Leu Met Ala Thr
1               5                   10                  15

Leu Tyr Ser Cys Asn Asn Thr Ser Glu Lys Ile Ser Ala Glu Lys Thr
            20                  25                  30

Glu Asp Lys Pro Glu Ile Ser Gln Val Asp Ile Asp Arg Leu Gly Ile
        35                  40                  45

Thr Asn Pro Asp Ser Leu Ser Ala Ala Ser Val Arg Ala Leu Asp Trp
    50                  55                  60

Pro Asp Val Gly Asn Glu Trp Phe Ile Glu Phe Ser Glu Leu Gln Pro
65                  70                  75                  80

Leu Lys Gly Asp Leu Ala Tyr Glu Glu Gly Val Val Arg Arg Asp Pro
                85                  90                  95

Ser Ala Leu Leu Lys His Asp Gly Lys Tyr Tyr Val Trp Tyr Thr Lys
            100                 105                 110

Ser Val Gly Pro Thr Gln Gly Phe Gly Gly Asp Ile Glu Asn Asp Lys
        115                 120                 125

Val Phe Pro Trp Asp Arg Cys Asp Ile Trp Tyr Ala Thr Ser Glu Asp
    130                 135                 140

Gly Trp Thr Trp Glu Glu Gln Gly Ile Ala Val Ala Arg Gly Glu Lys
145                 150                 155                 160

Gly Glu Tyr Asp Asp Arg Ser Val Phe Thr Val Glu Ile Met Glu Asp
                165                 170                 175
```

```
Lys Gly Lys Tyr Tyr Leu Ser Tyr Gln Thr Ile Gln Ser Pro Tyr Asn
            180                 185                 190

Val Arg Thr Lys Asn Gln Val Gly Leu Ala Trp Ala Asp Ser Pro Asn
            195                 200                 205

Gly Pro Trp Thr Lys Ser Lys Asp Pro Ile Leu Ser Pro Ala Asp Asn
            210                 215                 220

Gly Ile Trp Lys Gly Glu Glu Gln Asn Arg Phe Ala Val Glu Lys Lys
225                 230                 235                 240

Gly Asp Phe Asp Ser His Lys Val His Asp Pro Cys Ile Ile Pro Tyr
            245                 250                 255

Asn Gly Lys Tyr Tyr Leu Tyr Tyr Lys Gly Glu Gln Met Gly Glu Glu
            260                 265                 270

Ile Thr Phe Gly Gly Arg Gln Ile Arg His Gly Val Ala Ile Ala Asp
            275                 280                 285

Asn Pro Lys Gly Pro Tyr Val Lys Ser Ala Tyr Asn Pro Ile Ser Asn
            290                 295                 300

Ser Gly His Glu Ile Cys Val Trp Lys His Asn Gly Gly Ile Ala Ser
305                 310                 315                 320

Leu Ile Thr Thr Asp Gly Pro Glu Lys Asn Thr Ile Gln Trp Ala Pro
            325                 330                 335

Asp Gly Val Asn Phe Gly Ile Lys Ser Val Ile Lys Gly Ala Pro His
            340                 345                 350

Ala Ile Gly Leu Asn Arg Glu Leu Asn Thr Asp Glu Ser Glu Glu Pro
            355                 360                 365

Gly Ala Ile Leu Gly Trp Gly Leu Ser His Ile Tyr Asn Asn Ser Asp
370                 375                 380

Tyr Gln Ser Ile Met Arg Phe Ser Ser Lys Arg Thr Ser His Val
385                 390                 395                 400

Ala Lys Gly Glu Lys Ala Glu
            405

<210> SEQ ID NO 4
<211> LENGTH: 368
<212> TYPE: PRT
<213> ORGANISM: Saccharophagus degradans

<400> SEQUENCE: 4

Met Ser Asp Ser Lys Val Asn Lys Lys Leu Ser Lys Ala Ser Leu Arg
1               5                   10                  15

Ala Ile Glu Arg Gly Tyr Asp Glu Lys Gly Pro Glu Trp Leu Phe Glu
            20                  25                  30

Phe Asp Ile Thr Pro Leu Lys Gly Asp Leu Ala Tyr Glu Glu Gly Val
            35                  40                  45

Ile Arg Arg Asp Pro Ser Ala Val Leu Lys Val Asp Asp Glu Tyr His
            50                  55                  60

Val Trp Tyr Thr Lys Gly Glu Gly Glu Thr Val Gly Phe Gly Ser Asp
65                  70                  75                  80

Asn Pro Glu Asp Lys Val Phe Pro Trp Asp Lys Thr Glu Val Trp His
            85                  90                  95

Ala Thr Ser Lys Asp Lys Ile Thr Trp Lys Glu Ile Gly Pro Ala Ile
            100                 105                 110

Gln Arg Gly Ala Ala Gly Ala Tyr Asp Asp Arg Ala Val Phe Thr Pro
            115                 120                 125

Glu Val Leu Arg His Asn Gly Thr Tyr Tyr Leu Val Tyr Gln Thr Val
            130                 135                 140
```

```
Lys Ala Pro Tyr Leu Asn Arg Ser Leu Glu His Ile Ala Ile Ala Tyr
145                 150                 155                 160

Ser Asp Ser Pro Phe Gly Pro Trp Thr Lys Ser Asp Ala Pro Ile Leu
                165                 170                 175

Ser Pro Glu Asn Asp Gly Val Trp Asp Thr Asp Glu Asp Asn Arg Phe
            180                 185                 190

Leu Val Lys Glu Lys Gly Ser Phe Asp Ser His Lys Val His Asp Pro
        195                 200                 205

Cys Leu Met Phe Phe Asn Asn Arg Phe Tyr Leu Tyr Tyr Lys Gly Glu
    210                 215                 220

Thr Met Gly Glu Ser Met Asn Met Gly Gly Arg Glu Ile Lys His Gly
225                 230                 235                 240

Val Ala Ile Ala Asp Ser Pro Leu Gly Pro Tyr Thr Lys Ser Glu Tyr
                245                 250                 255

Asn Pro Ile Thr Asn Ser Gly His Glu Val Ala Val Trp Pro Tyr Lys
            260                 265                 270

Gly Gly Met Ala Thr Met Leu Thr Thr Asp Gly Pro Glu Lys Asn Thr
        275                 280                 285

Cys Gln Trp Ala Glu Asp Gly Ile Asn Phe Asp Ile Met Ser His Ile
    290                 295                 300

Lys Gly Ala Pro Glu Ala Val Gly Phe Phe Arg Pro Glu Ser Asp Ser
305                 310                 315                 320

Asp Asp Pro Ile Ser Gly Ile Glu Trp Gly Leu Ser His Lys Tyr Asp
                325                 330                 335

Ala Ser Trp Asn Trp Asn Tyr Leu Cys Phe Phe Lys Thr Arg Arg Gln
            340                 345                 350

Val Leu Asp Ala Gly Ser Tyr Gln Gln Thr Gly Asp Ser Gly Ala Val
        355                 360                 365

<210> SEQ ID NO 5
<211> LENGTH: 430
<212> TYPE: PRT
<213> ORGANISM: Pseudoalteromonas atlantica

<400> SEQUENCE: 5

Met Lys Tyr Trp Leu Ile Gly Ala Leu Ser Leu Ser Leu Thr Ala Cys
1               5                   10                  15

Asn Asn Thr Thr Met Glu Ser Glu Thr Arg Ala Ala Ser Thr Ser Val
                20                  25                  30

Ser Ala Pro Asn Lys Ala Tyr Ser Gln Ala Asp Tyr Ala Tyr Leu Ala
            35                  40                  45

Ile Ser Gln Pro Asp Thr Met Ser Ala Ala Ser Lys Arg Ala Leu Ala
        50                  55                  60

Arg Asn Tyr His Lys Asn Glu Gln Trp Phe Gly Glu Phe Arg His Glu
65                  70                  75                  80

Thr Leu Phe Gly Asp Phe Ala Phe Asp Pro Asn Val Ser Arg Arg Asp
                85                  90                  95

Pro Ser Lys Val Leu Lys Val Asp Asn Val Phe Tyr Thr Trp Tyr Thr
            100                 105                 110

Arg Thr Thr Gly Glu Ala Val Gly Phe Gly Thr Gly Asp Pro Asn Ala
        115                 120                 125

Lys Val Phe Pro Trp Asp Gln Ala Glu Ile Trp Tyr Ala Thr Ser Lys
    130                 135                 140

Asp Gly Tyr His Trp Gln Glu Lys Gly Arg Ala Leu Gly Thr Gly Asp
```

```
                145                 150                 155                 160
Val Gly Gln Phe Asp Asp Arg Ser Val Phe Thr Pro Glu Val Leu Ala
                    165                 170                 175

His Gln Gly Met Phe Tyr Leu Val Tyr Gln Ala Ile Lys Ala Pro Tyr
                    180                 185                 190

Leu Asn Arg Thr Lys Asn Thr Val Ala Met Ala Tyr Ser Ser Ser Pro
                    195                 200                 205

Asp Gly Pro Trp Arg Lys Leu Asp Ala Pro Ile Leu Thr Ala Ser Asp
                    210                 215                 220

Thr Gly Glu Trp Ala Gly Thr Gln Asp Asn Arg Phe Leu Val Lys Ser
225                 230                 235                 240

Gln Gly Asp Phe Asp Ser His Lys Val His Asp Pro Thr Leu Leu Phe
                    245                 250                 255

Tyr Arg Asp Lys Phe Tyr Leu Tyr Tyr Lys Gly Glu Arg Met Gly Glu
                    260                 265                 270

Arg Lys Thr Ala Gly Gly Arg Glu Ile Arg Trp Gly Val Ala Ile Ala
                    275                 280                 285

Asp Asn Pro Gln Gly Pro Tyr Ile Lys Ser Ala Phe Asn Pro Ile Thr
                    290                 295                 300

His Ser Gly His Glu Leu Cys Val Trp Gln Tyr Gln Asp Gly Ile Ala
305                 310                 315                 320

Ile Val Ser Ser His Asp Gly Pro Glu Lys Gln Thr Ile Gln Tyr Ala
                    325                 330                 335

Pro Asp Gly Ile Asn Phe Glu Val Met Ser Tyr Leu Pro Ser Val Pro
                    340                 345                 350

Ser Ala Ile Gly Leu Val Glu Ser Leu Asp Lys Asn Ala Tyr Pro Thr
                    355                 360                 365

Ala Gly Leu Glu Trp Gly Leu Tyr His Glu Tyr Val Ile Pro Pro Gly
                    370                 375                 380

Lys Thr Trp Met Ser Gly Ile Asn His Ile Lys Arg Phe Ser Phe Asn
385                 390                 395                 400

Ala Pro Asn Arg Val Ser Met Gln Gly Asp Ser Ile Gly Asn Thr Pro
                    405                 410                 415

Gln Asn Asn Ser Gly Glu Phe Ile Asn Lys Gln Ser Asp His
                    420                 425                 430

<210> SEQ ID NO 6
<211> LENGTH: 367
<212> TYPE: PRT
<213> ORGANISM: Paenibacillus sp.

<400> SEQUENCE: 6

Met Gly Met Lys Lys Glu Ser Ala Ala Thr Ile Arg Ala Lys Gln Tyr
1               5                   10                  15

Thr Lys Asn Ala Asp Trp Phe Cys Glu Phe Lys Tyr Glu Pro Val Glu
                20                  25                  30

Gly Leu Gly Tyr Glu Glu Gly Ile His Arg Arg Asp Pro Ser Ser Val
                35                  40                  45

Ile Lys Val Gly Asp Leu Tyr Tyr Val Trp Tyr Thr Lys Ser Val Gly
                50                  55                  60

Glu Ala Val Gly Phe Asn Thr Gly Asp Pro Asp Ser Lys Val Phe Pro
65                  70                  75                  80

Trp Asp Gln Ser Asp Val Trp Tyr Ala Thr Ser Pro Asp Gly Thr Thr
                85                  90                  95
```

```
Trp Thr Glu Arg Gly Met Ala Val Gly Arg Pro Lys Gly Ser Tyr
            100                 105                 110

Asp Asp Arg Ser Val Phe Thr Pro Glu Ile Leu His His Asp Gly Lys
        115                 120                 125

Phe Tyr Leu Val Tyr Gln Val Ile Glu Gly Gln Tyr Leu Leu Arg Lys
        130                 135                 140

Tyr Glu Asn Ile Ala Met Ala Val Ala Glu Ser Pro Glu Gly Pro Trp
145                 150                 155                 160

Arg Lys Leu Asp Ala Pro Ile Leu Arg Pro Ala Met Asn Gly Glu Trp
                165                 170                 175

Phe Gly Asp Asp Asp Asn Arg Leu Thr Val Lys His Lys Gly Asp Phe
            180                 185                 190

Asp Ser Leu Lys Val His Asp Pro Val Leu Phe Tyr Tyr Asn Asn Gln
        195                 200                 205

Phe Trp Leu Tyr Tyr Lys Gly Glu Gln Lys Gly Glu Glu Met Asn Phe
210                 215                 220

Gly Gly Arg Thr Thr Lys Trp Gly Val Ala Ile Ser Asp His Pro Glu
225                 230                 235                 240

Gly Pro Tyr Val Lys Ser Glu Tyr Asn Pro Val Thr Asn Ser Gly His
                245                 250                 255

Glu Thr Leu Leu Trp His Tyr Arg Gly Gly Met Ala Ala Leu Leu Ser
            260                 265                 270

Thr Asp Gly Pro Glu Lys Asn Thr Ile Gln Tyr Ala Pro Asp Gly Ile
        275                 280                 285

Asn Phe Glu Ile Glu Ala Val Ile Lys Asn Pro Pro Glu Ala Ala Gly
    290                 295                 300

Pro Phe Arg Thr Glu Asp Thr Asp Arg Ser Pro Leu Glu Gly Ile Arg
305                 310                 315                 320

Trp Gly Leu Cys His Asn Val His Thr Lys Trp Asn His Ile Leu Lys
                325                 330                 335

Phe Arg Thr Val Glu Asp Tyr Lys His Tyr Tyr Ala Asn Lys Ile Asn
            340                 345                 350

Pro Glu Val Leu Trp Leu Gly Lys Lys Ala Lys Gln Lys Lys Asp
        355                 360                 365

<210> SEQ ID NO 7
<211> LENGTH: 353
<212> TYPE: PRT
<213> ORGANISM: Ruminococcus sp.

<400> SEQUENCE: 7

Met Lys Leu Ser Ser Ala Ser Lys Arg Ala Ile Glu Arg Asn Tyr Tyr
1               5                   10                  15

Gln Ser Cys Glu Trp Phe Cys Asp Phe Lys Ser Gly Ile Glu Gly
            20                  25                  30

Ile Gly Tyr Glu Lys Gly Ile His Arg Arg Asp Pro Ser Ser Val Ile
        35                  40                  45

Lys Val Gly Asp Asp Tyr Phe Val Trp Tyr Ser Arg Ser Val Gly Pro
    50                  55                  60

His Lys Gly Phe His Thr Gly Asp Glu Ala Lys Val Phe Pro Trp
65                  70                  75                  80

Asp Tyr Cys Asp Ile Trp Tyr Ala Val Ser Leu Asp Gly Tyr Arg Trp
                85                  90                  95

Glu Glu Lys Gly Pro Ala Val Val Arg Gly Glu Arg Gly Ala Tyr Asp
            100                 105                 110
```

Asp Arg Ser Val Phe Thr Pro Glu Ile Leu Glu Tyr Glu Gly Lys Tyr
            115                 120                 125

Tyr Leu Val Tyr Gln Val Val Gln His Pro Tyr Val Asn Arg Ser Phe
        130                 135                 140

Glu Ser Ile Ala Ile Ala Val Ala Asp Ser Pro His Gly Pro Phe Thr
145                 150                 155                 160

Lys Ser Lys Glu Pro Ile Leu Thr Pro Thr Lys Asp Gly Ile Trp Glu
                165                 170                 175

Gly Glu Glu Asp Asn Arg Phe Ala Val Lys Lys Gly Ser Phe Asp
                180                 185                 190

Ser His Lys Val His Asp Pro Ile Leu Phe Ala Phe Arg Gly Lys Phe
                195                 200                 205

Tyr Leu Tyr Tyr Lys Gly Glu Pro Met Gly Glu Glu Leu Tyr Met Gly
        210                 215                 220

Gly Arg Glu Thr Lys Trp Gly Val Ala Ile Ala Asp Asn Ile Leu Gly
225                 230                 235                 240

Pro Tyr His Arg Ser Glu Tyr Asn Pro Val Thr Asn Ser Gly His Glu
                245                 250                 255

Thr Cys Leu Trp Gln Tyr Asn Gly Gly Ile Ala Ala Phe Leu Arg Thr
                260                 265                 270

Asp Gly Val Glu Lys Asn Thr Ile Gln Phe Ala Glu Asp Gly Ile Asn
                275                 280                 285

Phe Glu Ile Lys Ser Val Ile Lys Gln Gly Pro Glu Ala Cys Gly Pro
        290                 295                 300

Tyr Arg His Leu Glu Ser Asp Ser Asn Pro Leu Lys Gly Met Glu Trp
305                 310                 315                 320

Gly Leu Cys His Asp Val Ser Gln Asp Tyr Gly Phe Ile Lys Arg Phe
                325                 330                 335

Asp Ile Asp Glu Trp Gln Lys Lys Val Tyr Thr Asn Arg Glu Met Tyr
                340                 345                 350

Glu

<210> SEQ ID NO 8
<211> LENGTH: 364
<212> TYPE: PRT
<213> ORGANISM: Paenibacillus sp.

<400> SEQUENCE: 8

Met Arg Lys Glu Ser Ala Ala Thr Lys Arg Ala Lys Gln Tyr Thr Lys
1               5                   10                  15

Asn Ser Asp Trp Phe Cys Glu Phe Arg Ile Ser Pro Val Gln Gly Leu
                20                  25                  30

Gly Tyr Glu Glu Gly Val His Arg Arg Asp Pro Ser Ser Val Ile Lys
            35                  40                  45

Val Asn Asp Leu Tyr Tyr Val Trp Tyr Thr Lys Thr Glu Gly Glu Ala
        50                  55                  60

Ala Gly Phe Gln Thr Gly Asp Pro Asp Ala Lys Val Phe Pro Trp Asp
65                  70                  75                  80

Leu Ser Glu Val Trp Tyr Ala Thr Ser Pro Asp Gly Val Asn Trp Thr
                85                  90                  95

Glu Arg Gly Arg Ala Ile Gly Arg Gly Pro Lys Gly Ser Tyr Asp Asp
                100                 105                 110

Arg Ser Val Phe Thr Pro Glu Ile Leu His His Glu Asp Lys Phe Tyr
            115                 120                 125

Leu Val Tyr Gln Val Val Gln Ser Pro Tyr Thr Leu Arg Thr Leu Glu
            130                 135                 140

Asn Ile Ala Met Ala Val Ala Glu Ser Pro Glu Gly Pro Trp Arg Lys
145                 150                 155                 160

Leu Asp Glu Pro Ile Leu Arg Pro Ser Asn Asn Gly Glu Trp Phe Gly
                165                 170                 175

Asp Asp Asp Asn Arg Leu Thr Val Lys His Lys Gly Asp Phe Asp Ser
            180                 185                 190

Leu Lys Val His Asp Pro Thr Leu Phe Phe Tyr Asn Asn Gln Phe Trp
        195                 200                 205

Leu Tyr Tyr Lys Gly Glu Gln Met Gly Glu Met Asn Phe Gly Gly
        210                 215                 220

Arg Thr Thr Lys Trp Gly Val Ala Ile Ala Asp His Pro Glu Gly Pro
225                 230                 235                 240

Tyr Val Lys Ser Glu Tyr Asn Pro Ile Thr Asn Ser Gly His Glu Thr
                245                 250                 255

Cys Leu Trp Gln Tyr Arg Gly Gly Met Ala Ala Leu Leu Thr Thr Asp
            260                 265                 270

Gly Pro Glu Lys Asn Thr Ile Gln Tyr Ala Pro Asp Gly Ile Asn Phe
        275                 280                 285

Glu Ile Glu Ala Val Ile Lys Asn Pro Pro Glu Ala Pro Gly Pro Tyr
290                 295                 300

Arg Thr Pro Asp Ala Asp Arg Ser Pro Leu Glu Gly Leu Arg Trp Gly
305                 310                 315                 320

Leu Cys His Asn Val His Ser Lys Trp Asn Tyr Ile Gln Met Tyr Thr
                325                 330                 335

Val Asp Glu Ser Phe Lys His Tyr Tyr Met Asn Lys Ile Asn Pro Glu
            340                 345                 350

Glu Leu Trp Leu Gly Lys Ser Pro Lys Arg Asn Gln
        355                 360

<210> SEQ ID NO 9
<211> LENGTH: 382
<212> TYPE: PRT
<213> ORGANISM: Flavobacteriales bacterium

<400> SEQUENCE: 9

Met Lys Lys Glu Lys Glu Val Val Glu Lys Lys Ser Phe Glu Ile Ser
1               5                   10                  15

Asn Glu Gln Leu Asp Asn Leu Gly Ile Thr Asn Arg Asp Ser Leu Ser
            20                  25                  30

Ser Ala Ser Lys Arg Ala Leu Lys Trp Pro Asn Ile Gly Asn Glu Trp
        35                  40                  45

Phe Ile Glu Phe Ser Ala Leu Lys Pro Leu Lys Gly Asp Leu Ala Tyr
    50                  55                  60

Glu Glu Gly Val Val Arg Arg Asp Pro Ser Ala Leu Ile Phe Glu Asn
65                  70                  75                  80

Gly Lys Tyr Tyr Val Trp Tyr Ser Lys Ser Leu Gly Glu Ser Gln Gly
                85                  90                  95

Phe Gly Gly Asp Ile Glu Asn Asp Lys Val Phe Pro Trp Asp Arg Cys
            100                 105                 110

Asp Ile Trp Tyr Ala Thr Ser Val Asp Gly Trp Thr Trp Lys Glu Glu
        115                 120                 125

Gly Pro Ala Ile Val Arg Gly Val Asn Gly Glu Phe Asp Asp Arg Ser

```
            130                 135                 140
Val Phe Thr Val Glu Ile Met Lys Tyr Glu Asn Met Tyr Tyr Leu Cys
145                 150                 155                 160

Tyr Gln Thr Val Gln Ser Pro Tyr Thr Val Arg Val Lys Asn Gln Val
            165                 170                 175

Gly Leu Ala Trp Ser Asp Ser Pro Gly Pro Trp Thr Lys Ser Lys
            180                 185                 190

Gln Pro Ile Leu Ser Pro Ala Asp Asn Gly Ile Trp Lys Gly Leu Asp
            195                 200                 205

Gln Asn Arg Phe Ser Val Glu Lys Lys Gly Asp Phe Asp Ser His Lys
            210                 215                 220

Val His Asp Pro Cys Ile Ile Pro Tyr Asn Gly Lys Phe Tyr Leu Tyr
225                 230                 235                 240

Tyr Lys Gly Glu Gln Met Gly Glu Glu Ile Thr Phe Gly Gly Arg Gln
            245                 250                 255

Ile Arg His Gly Leu Ala Ile Ala Glu Asn Pro Gln Gly Pro Tyr Ile
            260                 265                 270

Lys Ser Pro Tyr Asn Pro Ile Ser Asn Ser Gly His Glu Ile Cys Val
            275                 280                 285

Trp Glu Tyr Lys Asp Gly Ile Ala Ser Leu Ile Thr Thr Asp Gly Pro
            290                 295                 300

Glu Lys Asn Thr Ile Gln Trp Ala Asn Asp Gly Ile Asn Phe Glu Ile
305                 310                 315                 320

Met Ala Val Ile Lys Gly Ala Pro His Ala Ile Gly Leu Asn Arg Asn
            325                 330                 335

Val Asp Asn Gly Lys Asn Pro Thr Glu Val Leu Arg Trp Gly Leu Ser
            340                 345                 350

His Val Tyr Asn Asn Ser Asp Tyr Gln Ser Ile Met Arg Phe Ser Ser
            355                 360                 365

Gln Leu Lys Thr Val His Thr Ala Lys Gly Glu Lys Ala Lys
            370                 375                 380

<210> SEQ ID NO 10
<211> LENGTH: 402
<212> TYPE: PRT
<213> ORGANISM: Bacteroides plebeius

<400> SEQUENCE: 10

Met Arg Lys Ile Ile Phe Ala Ala Gly Met Met Ser Leu Leu Ala Ala
1               5                   10                  15

Cys Gly Asn Thr Gly Asn Thr Gln Thr Ile Ala Val Asp Asp Thr Gln
            20                  25                  30

Asn Tyr Asp Glu Arg Lys Ala Asp Ser Leu Gly Ile Pro Lys Gly Asn
            35                  40                  45

Lys Leu Ser Ala Ala Met Lys Arg Ala Met Lys Trp Glu Asn His Asp
    50                  55                  60

Asn Lys Trp Phe Phe Glu Tyr Lys Met Glu Pro Leu Lys Gly Asp Leu
65                  70                  75                  80

Ala Tyr Glu Glu Gly Val Val Arg Arg Asp Pro Ser Ala Met Leu Lys
                85                  90                  95

Ile Gly Asp Thr Tyr Tyr Val Trp Tyr Ser Lys Ser Tyr Gly Pro Thr
            100                 105                 110

Gln Gly Phe Ala Gly Asp Ile Glu Lys Asp Lys Val Phe Pro Trp Asp
            115                 120                 125
```

```
Arg Cys Asp Ile Trp Tyr Ala Thr Ser Lys Asp Gly Leu Thr Trp Lys
    130                 135                 140

Glu Gln Gly Ile Ala Val Lys Arg Gly Glu Lys Gly Ala Tyr Asp Asp
145                 150                 155                 160

Arg Ser Val Phe Thr Pro Glu Val Met Glu Trp Lys Gly Lys Tyr Tyr
                165                 170                 175

Leu Cys Tyr Gln Ala Val Lys Ser Pro Tyr Thr Val Arg Val Lys Asn
                180                 185                 190

Thr Ile Gly Met Ala Cys Ala Asp Ser Pro Glu Gly Leu Trp Thr Lys
                195                 200                 205

Thr Asp Lys Pro Val Leu Glu Pro Ser Asp Thr Gly Glu Trp Glu Gly
210                 215                 220

Asp Glu Asp Asn Arg Phe Lys Val Val Ser Lys Gly Asp Phe Asp Ser
225                 230                 235                 240

His Lys Val His Asp Pro Cys Ile Ile Pro Tyr Asn Gly Lys Phe Tyr
                245                 250                 255

Met Tyr Tyr Lys Gly Glu Arg Met Gly Glu Glu Ile Thr Trp Gly Gly
                260                 265                 270

Arg Glu Ile Lys His Gly Val Ala Ile Ala Glu Asn Pro Met Gly Pro
                275                 280                 285

Tyr Val Lys Ser Glu Tyr Asn Pro Ile Ser Asn Ser Gly His Glu Val
290                 295                 300

Cys Val Trp Pro Tyr Lys Gly Gly Ile Ala Ser Leu Ile Thr Thr Asp
305                 310                 315                 320

Gly Pro Glu Lys Asn Thr Leu Gln Trp Ser Pro Asp Gly Ile Asn Phe
                325                 330                 335

Glu Ile Met Ser Val Val Lys Gly Ala Pro His Ala Ile Gly Leu Asn
                340                 345                 350

Arg Ser Ala Asp Ala Glu Lys Glu Pro Thr Glu Ile Leu Arg Trp Gly
                355                 360                 365

Leu Thr His Ile Tyr Asn Ser Ser Asp Tyr Gln Ser Ile Met Arg Phe
                370                 375                 380

Ser Thr Trp Thr Leu Gln Thr His Thr Ala Lys Gly Glu Ser Lys Glu
385                 390                 395                 400

Arg Lys

<210> SEQ ID NO 11
<211> LENGTH: 408
<212> TYPE: PRT
<213> ORGANISM: Microscilla sp.

<400> SEQUENCE: 11

Met Lys Ile Met Asn Val Lys Tyr Ser Thr Ile Gly Ala Met Thr Ala
1               5                   10                  15

Leu Leu Phe Phe Ala Ser Cys Gln Thr Pro Cys Pro Glu Glu Gln Glu
                20                  25                  30

Glu Asn Phe Glu Ile Thr Gln Asp Lys Ile Asp Tyr Leu Gly Ile Thr
                35                  40                  45

Asn Pro Asp Lys Leu Ser Ala Ala Ser Lys Arg Ala Leu Gln Trp Pro
50                  55                  60

Asp Ile Gly Asn Glu Trp Tyr Gly Glu Phe Gln Val Tyr Asp Leu Lys
65                  70                  75                  80

Gly Asp Leu Ala Tyr Glu Glu Gly Val Val Arg Arg Asp Pro Ser Ser
                85                  90                  95
```

| | | | | | | | | | | | |
|---|---|---|---|---|---|---|---|---|---|---|---|
|Ile|Ile|Lys|His|Asp|Gly|Lys|Tyr|Phe|Val|Trp|Tyr|Ser|Lys|Ser|Thr|
| | |   |100|   |   |   |105|   |   |   |   |110|   |   |   |

Ile Ile Lys His Asp Gly Lys Tyr Phe Val Trp Tyr Ser Lys Ser Thr
                100                 105                 110

Gly Lys Thr Asp Gly Phe Ala Gly Asp Ile Glu Lys Lys Val Phe
        115                 120                 125

Pro Trp Asp Arg Cys Asp Ile Trp Phe Ala Thr Ser Glu Asp Gly Trp
        130                 135                 140

Thr Trp Lys Glu Glu Gly Met Ala Val Gly Arg Gly Glu Lys Gly Thr
145                 150                 155                 160

Tyr Asp Asp Arg Ser Val Phe Thr Thr Glu Val Met Glu His Asn Gly
                165                 170                 175

Thr Tyr Tyr Leu Val Tyr Gln Thr Val Lys Ser Pro Tyr Asn Val Arg
                180                 185                 190

Val Lys Asn Gln Val Gly Leu Ala Trp Ser Asp Ser Pro Tyr Gly Pro
            195                 200                 205

Trp Thr Lys Ser Lys Glu Pro Ile Leu Ser Pro Ser Asp Asn Gly Ile
        210                 215                 220

Trp Lys Gly Asp Glu Asp Asn Arg Phe Leu Val Glu Lys Lys Gly Asp
225                 230                 235                 240

Phe Asp Ser His Lys Val His Asp Pro Cys Ile Ile Pro Tyr Asn Gly
                245                 250                 255

Lys Phe Tyr Leu Tyr Tyr Lys Gly Glu Gln Met Gly Glu Gln Ile Thr
                260                 265                 270

Phe Gly Gly Arg Gln Ile Arg His Gly Val Ala Ile Ala Asp Asp Pro
            275                 280                 285

Lys Gly Pro Tyr Val Lys Ser Pro Tyr Asn Pro Ile Ser Asn Ser Gly
        290                 295                 300

His Glu Ile Cys Val Trp Lys His Glu Gly Gly Ile Ala Ser Leu Ile
305                 310                 315                 320

Thr Thr Asp Gly Pro Glu Arg Asn Thr Ile Gln Trp Ala Pro Asp Gly
                325                 330                 335

Ile Asn Phe Asp Ile Ile Ala Ala Ile Pro Gly Ala Pro His Ala Ile
            340                 345                 350

Gly Leu Asn Arg Thr Leu Asn Asn Glu Asp Pro Phe Gly Ile Phe Gly
        355                 360                 365

Trp Gly Leu Thr His Glu Tyr Val Thr Tyr Asp Trp Gln Tyr Ile Arg
370                 375                 380

Arg Phe Glu Gly Lys Arg Lys Thr Thr His Val Ala Arg Gly Glu Thr
385                 390                 395                 400

Gly Ser Lys Lys Ser Ser Asp Glu
                405

<210> SEQ ID NO 12
<211> LENGTH: 1107
<212> TYPE: DNA
<213> ORGANISM: Saccharophagus degradans

<400> SEQUENCE: 12
atgagcgatt caaaagtaaa taaaaaattg agtaaagcta gcctgcgagc catagagcgc         60
ggctacgatg aaaaggggcc tgaatggctg tttgagtttg atattccccc actaaaaggc        120
gacttagcct acgaagaagg cgtaattcgt cgagacccca gcgcagtatt aaaggtggac        180
gatgaatatc acgtttggta caccaagggc gaaggtgaaa cagtaggctt cggcagcgac        240
aaccccgaag acaagtcttc ccatgggat aaaacagaag tttggcacgc cacctctaaa         300
gataagatta cttggaaaga aattggccct gccatacaac gcggcgcagc tgggcatat         360

```
gatgaccgtg cagtgttcac ccccgaagtc ctgcgccata acggcaccta ctaccttgta    420
tatcaaacgg taaaagcgcc ctacttaaac cgatcgctag agcatatagc catcgcatac    480
agcgattccc cctttggccc atggaccaaa tccgatgcgc caattttaag cccagaaaat    540
gacggcgttt gggatacgga cgaagacaat cgattttag taaaagagaa aggcagtttc    600
gatagccaca aagtacacga ccctgctta atgttttta caatcgtttt ctacctgtat    660
tacaaaggcg agactatggg cgaaagcatg aacatgggcg gcagagaaat aaaacacggt    720
gtagccattg ccgactcgcc acttgggccc tacaccaaaa gcgaatacaa ccctattacc    780
aatagtggcc atgaagttgc cgtatggccc tacaaaggtg aatggccac catgctaacc    840 accgacgggc cagaaaaaaa cacctgccag tgggcagaag acggcattaa ctttgacatt    900
atgtcgcata taaaaggcgc accagaagca gtaggttttt ttagaccaga aagcgatagc    960
gacgacccta taagcggcat tgaatggggg ctaagccaca agtacgacgc cagctggaac   1020
tggaactatc tatgcttttt taaaacgcgt cgacaagttt tagatgcagg tagctatcag   1080
caaacaggcg attccggagc agtataa                                        1107
```

<210> SEQ ID NO 13
<211> LENGTH: 21
<212> TYPE: PRT
<213> ORGANISM: Artificial Sequence
<220> FEATURE:
<223> OTHER INFORMATION: Motif 1
<220> FEATURE:
<221> NAME/KEY: VARIANT
<222> LOCATION: (1)..(21)
<223> OTHER INFORMATION: With a left-to-right direction of sequence, the
      square brackets of [IV], [AS], [WF], [KET] and [KR] are omitted.
      [ ] means "or". So, [IV] is I or V. And X means any amino acid.
<220> FEATURE:
<221> NAME/KEY: misc_feature
<222> LOCATION: (12)..(12)
<223> OTHER INFORMATION: Xaa can be any naturally occurring amino acid

<400> SEQUENCE: 13

Ile Val Gly Val Ala Val Ala Ser Asp Ser Pro Xaa Gly Pro Trp Phe
1               5                   10                  15

Lys Glu Thr Lys Arg
            20

<210> SEQ ID NO 14
<211> LENGTH: 24
<212> TYPE: PRT
<213> ORGANISM: Artificial Sequence
<220> FEATURE:
<223> OTHER INFORMATION: Motif 2
<220> FEATURE:
<221> NAME/KEY: VARIANT
<222> LOCATION: (1)..(24)
<223> OTHER INFORMATION: With a left-to-right direction of sequence, the
      square brackets of [ATN], [IV], [LY], [DN], [YF], [LM], [YF], and
      [YF] are omitted. [ ] means "or".  So, [ATN] is A or T or N.

<400> SEQUENCE: 14

Ala Thr Asn Pro Glu Ile Val Leu Tyr Glu His Asp Asn Gly Lys Tyr
1               5                   10                  15

Phe Tyr Leu Met Tyr Phe Tyr Phe
            20

<210> SEQ ID NO 15
<211> LENGTH: 28
<212> TYPE: PRT

```
<213> ORGANISM: Artificial Sequence
<220> FEATURE:
<223> OTHER INFORMATION: Motif 3
<220> FEATURE:
<221> NAME/KEY: VARIANT
<222> LOCATION: (1)..(28)
<223> OTHER INFORMATION: With a left-to-right direction of sequence, the
      square brackets of [TI], [AS], [SD], [PI], [LE], [YF], and [IV]
      are omitted. [ ] means "or".  So, [TI] is T or I. And X means any
      amino acid.
<220> FEATURE:
<221> NAME/KEY: misc_feature
<222> LOCATION: (24)..(24)
<223> OTHER INFORMATION: Xaa can be any naturally occurring amino acid

<400> SEQUENCE: 15

Val Gly Val Ala Thr Ile Ala Ser Asp Ser Asp Pro Ile Leu Glu Gly
1               5                   10                  15

Pro Tyr Phe Thr Lys Ser Glu Xaa Asn Pro Ile Val
            20                  25

<210> SEQ ID NO 16
<211> LENGTH: 71
<212> TYPE: PRT
<213> ORGANISM: Artificial Sequence
<220> FEATURE:
<223> OTHER INFORMATION: Motif 4
<220> FEATURE:
<221> NAME/KEY: VARIANT
<222> LOCATION: (1)..(71)
<223> OTHER INFORMATION: With a left-to-right direction of sequence, the
      square brackets of [TIV], [VL], [WF], [PQ], [YF], [GD], [IM],
      [AS], [LI], [YWF], [PE], [IV], [ED], [MK], [AS], [VH], [GN], [AP],
      and [EH] are omitted. [ ] means "or".  So, [TIV] is T or I or V.

<400> SEQUENCE: 16

Asn Ser Gly His Glu Thr Ile Val Cys Val Leu Trp Phe Pro Gln Tyr
1               5                   10                  15

Phe Lys Gly Asp Gly Ile Met Ala Ala Ser Leu Leu Ile Thr Thr Asp
            20                  25                  30

Gly Pro Glu Lys Asn Thr Ile Gln Tyr Trp Phe Ala Pro Glu Asp Gly
        35                  40                  45

Ile Val Asn Phe Glu Asp Ile Met Lys Ala Ser Val His Ile Lys Gly
    50                  55                  60

Asn Ala Pro Pro Glu His Ala
65                  70

<210> SEQ ID NO 17
<211> LENGTH: 15
<212> TYPE: PRT
<213> ORGANISM: Artificial Sequence
<220> FEATURE:
<223> OTHER INFORMATION: Motif 5
<220> FEATURE:
<221> NAME/KEY: VARIANT
<222> LOCATION: (1)..(15)
<223> OTHER INFORMATION: With a left-to-right direction of sequence, the
      square brackets of [AY], [GL], [VI], and [TN] are omitted.
      [ ] means "or".  So, [AY] is A or Y.

<400> SEQUENCE: 17

Ala Tyr Thr Ser Lys Asp Gly Leu Val Ile Thr Asn Trp Lys Glu
1               5                   10                  15

<210> SEQ ID NO 18
<211> LENGTH: 29
<212> TYPE: PRT
<213> ORGANISM: Artificial Sequence
```

```
<220> FEATURE:
<223> OTHER INFORMATION: Motif 6
<220> FEATURE:
<221> NAME/KEY: VARIANT
<222> LOCATION: (1)..(29)
<223> OTHER INFORMATION: With a left-to-right direction of sequence, the
      square brackets of [DE], [SP], [VI], [IL], [EV], [GD], [VM], and
      [ST] are omitted. [ ] means "or".  So, [DE] is D or E. And X means
      any amino acid.
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 18

Val Xaa Arg Arg Asp Glu Pro Ser Pro Ser Val Ile Ile Leu Lys Glu
1               5                   10                  15

Val Asp Gly Asp Xaa Tyr Tyr Val Met Trp Tyr Ser Thr
            20                  25

<210> SEQ ID NO 19
<211> LENGTH: 75
<212> TYPE: PRT
<213> ORGANISM: Artificial Sequence
<220> FEATURE:
<223> OTHER INFORMATION: Motif 7
<220> FEATURE:
<221> NAME/KEY: VARIANT
<222> LOCATION: (1)..(75)
<223> OTHER INFORMATION: With a left-to-right direction of sequence, the
      parentheses of [FL], [LT], [KV], [SH], [KQ], [DS], [HL], [CIT],
      [FL], [FP], [FY], [NR], [GN], [KQR], [YW], [QRT], [NT], [FAM],
      [ET], [IT], and [KR] are omitted. [ ] means "or".  So, [FL] is F
      or L.

<400> SEQUENCE: 19

Asp Asn Arg Phe Leu Leu Thr Val Lys Val Ser His Lys Gln Gly Asp
1               5                   10                  15

Ser Phe Asp Ser His Leu Lys Val His Asp Pro Cys Ile Thr Leu Phe
            20                  25                  30

Leu Phe Pro Phe Tyr Asn Arg Gly Asn Lys Gln Arg Phe Tyr Trp Leu
        35                  40                  45

Tyr Tyr Lys Gly Glu Gln Arg Thr Met Gly Glu Met Asn Thr Phe
    50                  55                  60

Ala Met Gly Gly Arg Glu Thr Ile Thr Lys Arg
65                  70                  75

<210> SEQ ID NO 20
<211> LENGTH: 31
<212> TYPE: PRT
<213> ORGANISM: Artificial Sequence
<220> FEATURE:
<223> OTHER INFORMATION: Motif 14
<220> FEATURE:
<221> NAME/KEY: VARIANT
<222> LOCATION: (1)..(31)
<223> OTHER INFORMATION: With a left-to-right direction of sequence, the
      square brackets of [TG], [DG], [DI], [PE], [DN], [DA], [CS], [DE],
      [IV], and [YH] are omitted. [ ] means "or".  So, [TG] is T or G.

<400> SEQUENCE: 20

Gly Phe Gly Thr Gly Asp Gly Asp Ile Pro Glu Asp Asn Asp Ala Lys
1               5                   10                  15

Val Phe Pro Trp Asp Arg Cys Ser Asp Glu Ile Val Trp Tyr His
```

-continued

```
              20                  25                  30

<210> SEQ ID NO 21
<211> LENGTH: 29
<212> TYPE: PRT
<213> ORGANISM: Artificial Sequence
<220> FEATURE:
<223> OTHER INFORMATION: Motif 16
<220> FEATURE:
<221> NAME/KEY: VARIANT
<222> LOCATION: (1)..(29)
<223> OTHER INFORMATION: With a left-to-right direction of sequence, the
      square brackets of [DEK], [QAEK], [IL], [RS], [GS], [DN], [DTN],
      [EIS], and [GD] are omitted. [ ] means "or".  So, [DEK] is D or E
      or K.

<400> SEQUENCE: 21

Asp Glu Lys Gln Ala Glu Lys Pro Ile Leu Leu Arg Ser Pro Gly Ser
 1               5                  10                  15

Asp Asn Asp Thr Asn Gly Glu Ile Ser Trp Asp Gly Asp
             20                  25

<210> SEQ ID NO 22
<211> LENGTH: 21
<212> TYPE: PRT
<213> ORGANISM: Artificial Sequence
<220> FEATURE:
<223> OTHER INFORMATION: Motif 17
<220> FEATURE:
<221> NAME/KEY: VARIANT
<222> LOCATION: (1)..(21)
<223> OTHER INFORMATION: With a left-to-right direction of sequence, the
      square brackets of [IVL], [KP], [SA], [YF], and [SA] are omitted.
      [ ] means "or". So, [IVL] is I or V or L.

<400> SEQUENCE: 22

Ile Val Leu Gly Arg Gly Glu Lys Pro Gly Ser Ala Tyr Phe Asp Asp
 1               5                  10                  15

Arg Ser Ala Val Phe
             20

<210> SEQ ID NO 23
<211> LENGTH: 58
<212> TYPE: PRT
<213> ORGANISM: Artificial Sequence
<220> FEATURE:
<223> OTHER INFORMATION: Motif 20
<220> FEATURE:
<221> NAME/KEY: VARIANT
<222> LOCATION: (1)..(58)
<223> OTHER INFORMATION: With a left-to-right direction of sequence, the
      square brackets of [LP], [YFN], [NPST], [ELP], [DES], [DKR],
      [ENS], [LT], [EA], [GI], [LI], [RE], [CS], [DIKN], [YV], [NDH],
      [SAN], [SK], and [WD] are omitted. [ ] means "or".  So, [LP] is L
      or P.

<400> SEQUENCE: 23

Gly Leu Pro Tyr Phe Asn Arg Asn Pro Ser Thr Glu Leu Pro Asp Ala
 1               5                  10                  15

Asp Glu Ser Asp Lys Arg Glu Asn Ser Pro Leu Thr Glu Ala Gly Ile
             20                  25                  30

Leu Ile Arg Glu Trp Gly Leu Cys Ser His Asp Ile Lys Asn Tyr Val
         35                  40                  45

Asn Asp His Ser Ala Asn Ser Lys Trp Asp
     50                  55

<210> SEQ ID NO 24
```

```
<211> LENGTH: 22
<212> TYPE: PRT
<213> ORGANISM: Artificial Sequence
<220> FEATURE:
<223> OTHER INFORMATION: Motif 34
<220> FEATURE:
<221> NAME/KEY: VARIANT
<222> LOCATION: (1)..(22)
<223> OTHER INFORMATION: With a left-to-right direction of sequence, the
      square brackets of [TVA], [VI], [QK], [SA], [TLN], [NVL], and
      [STV] are omitted. [ ] means "or".  So, [TVA] is T or V or A.

<400> SEQUENCE: 24

Gln Thr Val Ala Val Ile Gln Lys Ser Ala Pro Tyr Thr Leu Asn Asn
1               5                   10                  15

Val Leu Arg Ser Thr Val
            20

<210> SEQ ID NO 25
<211> LENGTH: 11
<212> TYPE: PRT
<213> ORGANISM: Artificial Sequence
<220> FEATURE:
<223> OTHER INFORMATION: Motif 40

<400> SEQUENCE: 25

Pro Leu Lys Gly Asp Leu Ala Tyr Glu Glu Gly
1               5                   10
```